US007902344B2

(12) United States Patent
Harvey et al.

(10) Patent No.: US 7,902,344 B2
(45) Date of Patent: Mar. 8, 2011

(54) ANTIBODIES WITH INCREASED AFFINITIES FOR ANTHRAX ANTIGENS

(75) Inventors: Barrett R. Harvey, Austin, TX (US); George Georgiou, Austin, TX (US); Brent L. Iverson, Austin, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 1294 days.

(21) Appl. No.: 11/179,244

(22) Filed: Jul. 12, 2005

(65) Prior Publication Data

US 2005/0267294 A1 Dec. 1, 2005

Related U.S. Application Data

(62) Division of application No. 10/620,049, filed on Jul. 15, 2003, now Pat. No. 6,916,474.

(60) Provisional application No. 60/396,058, filed on Jul. 15, 2002.

(51) Int. Cl.
*C07H 21/02* (2006.01)
*C07H 21/04* (2006.01)
*A61K 39/395* (2006.01)
*A61K 39/00* (2006.01)
*A61K 39/02* (2006.01)
*A61K 39/07* (2006.01)

(52) U.S. Cl. ............... 536/23.1; 536/23.7; 424/130.1; 424/134.1; 424/135.1; 424/184.1; 424/236.1; 424/246.1

(58) Field of Classification Search ............... None
See application file for complete search history.

(56) References Cited

U.S. PATENT DOCUMENTS

| 5,601,823 A | 2/1997 | Williams et al. | 424/167.1 |
|---|---|---|---|
| 6,329,156 B1 | 12/2001 | Cirino et al. | 435/7.21 |
| 6,916,474 B2 | 7/2005 | Harvey et al. | 424/130.1 |

FOREIGN PATENT DOCUMENTS
WO    WO 2005/023177    3/2005

OTHER PUBLICATIONS

Maynard et al (Nature Biotechnology, Jun. 2002)See Harlow and Lane, (Antibodies, A laboratory Manual, Cold Springs Harbor Laboratory Publications, 1988).*
Maynard et al (Nature Biotechnology, Jun. 2002).*
Greenspan et al. (Nature Biotechnology 17: 936-937, 1999).*
Cirino et al., "Disruption of anthrax toxin binding with the use of human antibodies and competitive inhibitors," *Infection and Immunity*, 67:2957-2963, 1999.
Maynard et al., In: Abstracts of Papers of 216th National Meeting of the ACS, Boston, Massachusetts, #212, BIOT, Aug. 23-27, 1998.
Castillo et al., "T7 displayed peptides as targets for selecting peptide specific scFvs from M13 scFv display libraries," *J. Immunol. Methods*, 257:117-122, 2001.
Knappik et al., "Fully synthetic human combinatorial antibody libraries (HuCAL) based on modular consensus frameworks and CDRs randomized with trinucleotides," *J. Mol. Biol.*, 296:57-86, 2000.
Stemmer, "Rapid evolution of a protein in vitro DNA shuffling," *Nature*, 370:389-391, 1994.
Walroy et al., "Comparison of four serological methods for the detection of diphtheria anti-toxin antibodies," *J. Immunol. Methods*, 245:55-65, 2000.
Bradley et al., *Nature*, "Identification of the cellular receptor for anthrax toxin," 8;414(6860):225-229, 2001.
Bull and Parrich, "A binding contract for anthrax," *Science*, 297:201-202, 202, 2002.
Chen and Okayama, "High-efficiency transformation of mammalian cells by plasmid DNA," *Mol. Cell Biol.*, 7(8):2745-2752, 1987.
Chen et al., "Isolation of high-affinity ligand-binding proteins by periplasmic expression with cyto metric screening," *Nat. Biotechnol.*, 19:537-542, 2001.
Chen et al., "In vitro scanning saturation mutagenesis of all the specificity determining residues in an antibody binding site," *Protein Eng.*, 12:349-356, 1999.
Creighton, *Protein Structure: A Practical Approach*, p. 184-186, 1994.
Creighton, *Proteins: Structures and Molecular Properties*, p. 314-315, 1984.
Daughterty et al., "Quantitative analysis of the effect of the mutation frequency on the affinity maturation of antibodies," *Proc. Natl. Acad. Sci.*, USA, 97:2029-2034, 2000.
Ezzell et al., "Immunoelectrophoretic analysis, toxicity, and kinetics of in vitro production of the protective antigen and lethal factor components of *Bacillus anthracis* toxin," *Infect. Immun.*, 45:761-777, 1984.
Georgiou et al., "Display of heterologous proteins on the surface of microorganisms: from the screening of combinatorial libraries to live recombinant vaccines," *Nat. Biotechnol.*, 15:29-34, 1997.
Hayhurst and Georgiou,. "High throughput isolation," *Curr. Opin. Chem. Biol.*, 5:683-689, 2001.
Hayhurst and Harris, "*Escherichia coli* Skp chaperone coexpression improves solubility and phage display of single-chain antibody fragments," *Protein Expr. Purif.*, 15:336-343, 1999.
Hayhurst et al., "Isolation and expression of recombinant antibody fragments to the biological warfare pathogen *Brucella melitensis*," *J. Immunol. Methods*, 276:185-196, 2003.
Hayhurst, "mproved expression characteristics of single-chain Fv fragments when fused downstream of the *Escherichia coli* maltose-binding protein or upstream of a single immunoglobulin-constant domain," *Protein Expr. Purif.*, 18:1-10, 2000.
Hoess, "Protein design and phage display," *Chem. Rev.*, 101:3205-3218, 2001.
Ivins et al., "Influence of body weight on response of Fischer 344 rats to anthrax lethal toxin," *Applies and Environmental Microbiology*, 55:2098-2100, 1989.

(Continued)

*Primary Examiner* — Vanessa L. Ford
(74) *Attorney, Agent, or Firm* — Fulbright & Jaworski L.L.P.

(57) ABSTRACT

The invention overcomes the deficiencies of the prior art by providing antibody compositions having improved affinities for *Bacillus anthracis* antigens. The compositions have important thereapeutic and diagnostic applications, including treatment or detection of infection by *Bacillus anthracis*.

5 Claims, 6 Drawing Sheets

OTHER PUBLICATIONS

Keller and Stiehm, "Passive immunity in prevention and treatment of infectious diseases," *Clin. Microbiol. Reviews*, 13:602-614, 2000.

Krebber et al., "Reliable cloning of functional antibody variable domains from hybridomas and spleen cell repertoires employing a reengineered phage display system,"*J. Immunol. Methods*, 201:35-55, 1997.

Leppla, "Anthrax toxin," Chapter 19 In: *Handbook of Experimental Pharmacology*, 145:445-472, 2000.

Li et al., "X-ray snapshots of the maturation of an antibody response to a protein antigen," *Nat. Struct. Biol.*, 10(6):482-488, 2003.

Little et al., "Characterization of lethal factor binding and cell receptor binding domains of protective antigen of *Bacillus antracis* using monoclonal antibodies," *Microbiology*, 142:707-715, 1996.

Little et al., "Passive protection by polyclonal antibodies against *Bacillus antracis* infection in guinea pigs," *Infection and Immunity*, 65:5171-5175, 1997.

Little et al., "Production and characterization of monoclonal antibodies to the protective antigen component of *Bacillus anthracis* toxin," *Infect. Immun.*, 56:1807-1813, 1988.

Maynard et al., "Protection against anthrax toxin by recombinant antibody fragments correlates with antigen affinity," *Nat. Biotechnol.*, 20:597-601, 2002.

Maynard et al., *Nature Biotechnology*, vol. 20, 2002.

Mourez et al., "Designing a polyvalent inhibitor of anthrax toxin," *Nature Biotechnology*, 19:958-961, 2001.

Nosoh et al., *Protein Stability and Stabilization through Protein Engineering*, Chapter 7, p. 197, 1991.

Pitt et al., "In vitro correlate of immunity in a rabbit model of inhalational anthrax," Vaccine, 19:4768-4773, 2001.

Sellman et al., "Dominant-negative mutants of a toxin subunit: an approach to therapy of anthrax," *Science*, 292:695-697, 2001.

Singh et al., "A dominant negative mutant of *Bacillus antracis* protective antigen inhibits anthrax toxin in vivo," *J. of Biol. Chem.*, 276:22090-22094, 2001.

Turnbill et al., "Antibodies to Anthrax Toxin in Humans and Guinea Pigs and Their Relevance to Protective Immunity," Abstract, *Med. Microbiol. Immunol.*, 177:293-303, 1988.

U.S. Appl. No. 10/288,269, filed Nov. 5, 2002.

Wittrup, "The single cell as a microplate well," *Nat. Biotechnol.*, 18:1039-1040, 2000.

* cited by examiner

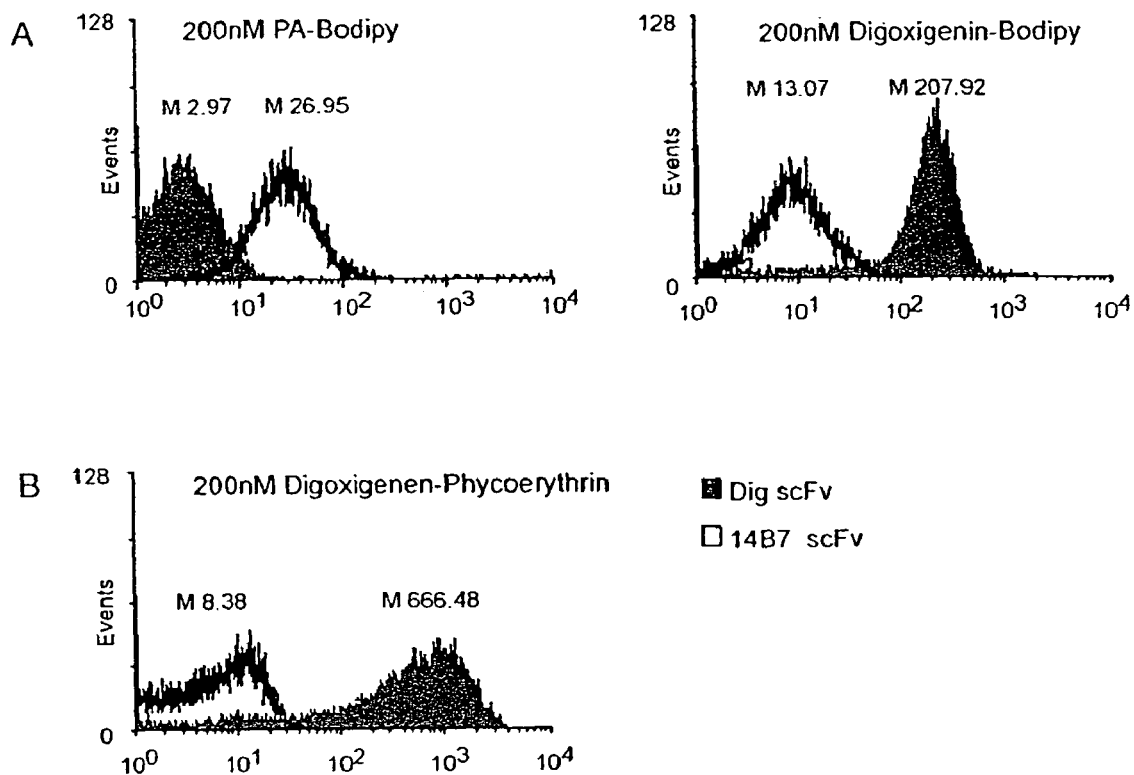
FIG. 2A, B

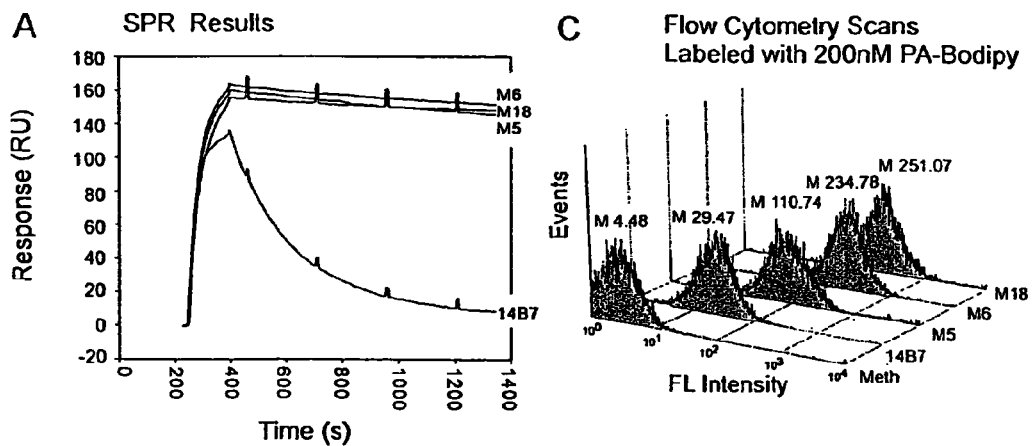
FIG. 3A-C

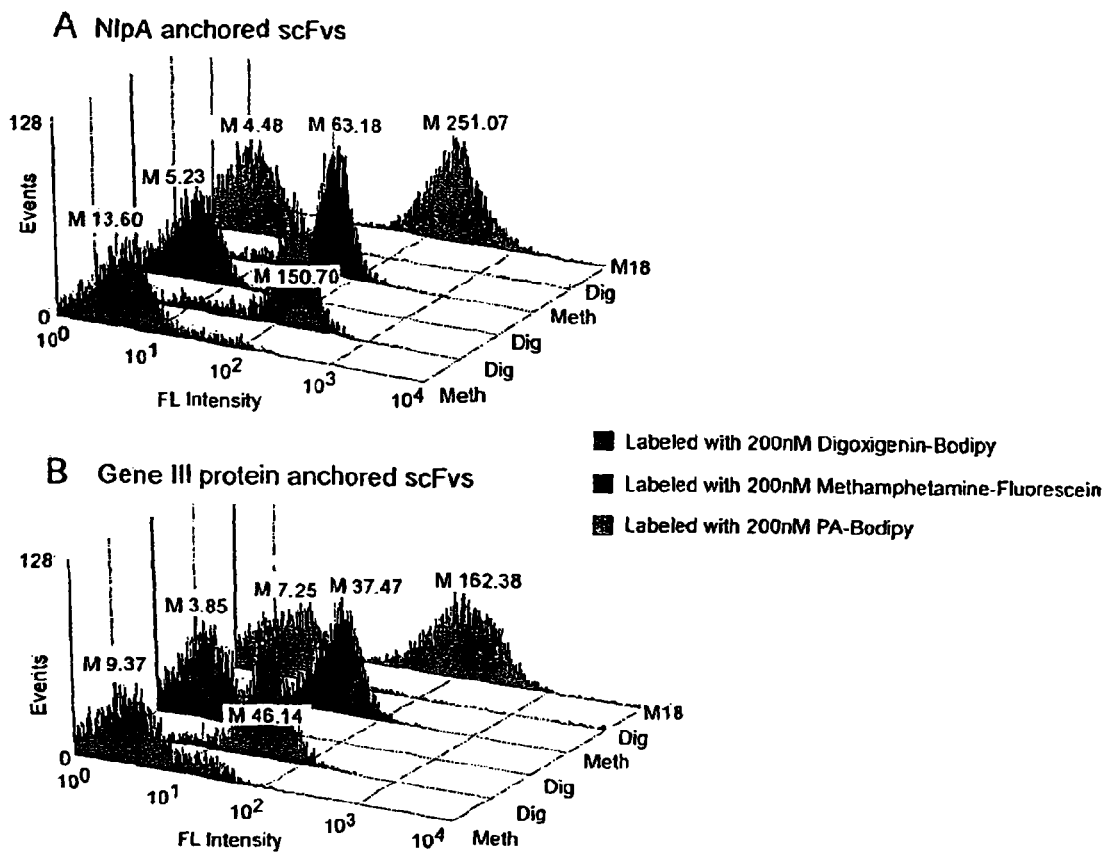
FIG. 4A, B

ANTIBODIES WITH INCREASED AFFINITIES FOR ANTHRAX ANTIGENS

This application is a divisional of U.S. Patent Application Ser. No. 10/620,049, filed Jul. 15, 2003, now U.S. Pat. No. 6,916,474 which application claims the priority of U.S. Provisional Patent App. No. 60/396,058, filed Jul. 15, 2002, the entire disclosures of which are incorporated herein by reference.

This invention was made with government support under contract number DAAD19-99-1-0207 awarded by the Army Research Office, and contract number DAAD17-01-D-0001 awarded by the Army Research Laboratory. The government has certain rights in the invention.

BACKGROUND OF THE INVENTION

1. Field of the Invention

The present invention relates generally to the field of protein engineering. More particularly, it concerns antibodies that immunologically bind with improved affinity to a *Bacillus anthracis* antigen.

2. Description of Related Art

The isolation of polypeptides that either bind to ligands with high affinity and specificity or catalyze the enzymatic conversion of a reactant (substrate) into a desired product is a key process in biotechnology. Ligand-binding polypeptides, including proteins and enzymes with a desired substrate specificity can be isolated from large libraries of mutants, provided that a suitable screening method is available. Small protein libraries composed of $10^3$-$10^5$ distinct mutants can be screened by first growing each clone separately and then using a conventional assay for detecting clones that exhibit specific binding. For example, individual clones expressing different protein mutants can be grown in microtiter well plates or separate colonies on semisolid media such as agar plates. To detect binding the cells are lysed to release the proteins and the lysates are transferred to nylon filters, which are then probed using radiolabeled or fluorescently labeled ligands (DeWildt et al. 2000). However, even with robotic automation and digital image systems for detecting binding in high density arrays, it is not feasible to screen large libraries consisting of tens of millions or billions of clones. The screening of libraries of that size is required for the de novo isolation of enzymes or protein binders that have affinities in the sub-nanomolar range.

The screening of very large protein libraries has been accomplished by a variety of techniques that rely on the display of proteins on the surface of viruses or cells. The underlying premise of display technologies is that proteins engineered to be anchored on the external surface of biological particles (i.e., cells or viruses) are directly accessible for binding to ligands without the need for lysing the cells. Viruses or cells displaying proteins with affinity for a ligand can be isolated in a variety of ways including sequential adsorption/desorption form immobilized ligand, by magnetic separations or by flow cytometry (U.S. Pat. Nos. 5,223,409, 5,837,500, Georgiou et al. 1997, Shusta et al. 1999).

The most widely used display technology for protein library screening applications is phage display. Phage display is a well-established and powerful technique for the discovery of proteins that bind to specific ligands and for the engineering of binding affinity and specificity (Rodi and Makowski, 1999). In phage display, a gene of interest is fused in-frame to phage genes encoding surface-exposed proteins, most commonly pIII. The gene fusions are translated into chimeric proteins in which the two domains fold independently. Phage displaying a protein with binding affinity for a ligand can be readily enriched by selective adsorption onto immobilized ligand, a process known as "panning". The bound phage is desorbed from the surface, usually by acid elution, and amplified through infection of *E. coli* cells. Usually, 4-6 rounds of panning and amplification are sufficient to select for phage displaying specific polypeptides, even from very large libraries with diversities up to $10^{10}$. Several variations of phage display for the rapid enrichment of clones displaying tightly binding polypeptides have been developed (Duenas and Borrebaeck, 1994; Malmborg et al., 1996; Kjaer et al., 1998; Burioni et al., 1998; Levitan, 1998; Mutuberria et al., 1999; Johns et al., 2000).

One of the most significant applications of phage display technology has been the isolation of high affinity antibodies (Dall'Acqua and Carter, 1998; Hudson et al., 1998; Hoogenboom et al., 1998; Maynard and Georgiou, 2000). Very large and structurally diverse libraries of scFv or $F_{AB}$ fragments have been constructed and have been used successfully for the in vitro isolation of antibodies to a multitude of both synthetic and natural antigens (Griffith et al., 1994; Vaughan et al., 1996; Sheets et al., 1998; Pini et al., 1998; de Haard et al., 1999; Knappik et al., 2000; Sblattero and Bradbury, 2000). Antibody fragments with improved affinity or specificity can be isolated from libraries in which a chosen antibody had been subjected to mutagenesis of either the CDRs or of the entire gene CDRs (Hawkins et al., 1992; Thompson et al., 1996; Chowdhury and Pastan, 1999). Finally, the expression characteristics of scFv, notorious for their poor solubility, have also been improved by phage display of mutant libraries (Deng et al., 1994; Coia et al., 1997).

However, several spectacular successes notwithstanding, the screening of phage-displayed libraries can be complicated by a number of factors. First, phage display imposes minimal selection for proper expression in bacteria by virtue of the low expression levels of antibody fragment gene III fusion necessary to allow phage assembly and yet sustain cell growth (Krebber et al., 1996, 1997). As a result, the clones isolated after several rounds of panning are frequently difficult to produce on a preparative scale in *E. coli*. Second, although phage displayed proteins may bind a ligand, in some cases their un-fused soluble counterparts may not (Griep et al., 1999). Third, the isolation of ligand-binding proteins and more specifically antibodies having high binding affinities can be complicated by avidity effects by virtue of the need for gene III protein to be present at around 5 copies per virion to complete phage assembly. Even with systems that result in predominantly monovalent protein display, there is nearly always a small fraction of clones that contain multiple copies of the protein. Such clones bind to the immobilized surface more tightly and are enriched relative to monovalent phage with higher affinities (Deng et al., 1995; MacKenzie et al., 1996, 1998). Fourth, theoretical analysis aside (Levitan, 1998), panning is still a "black box" process in that the effects of experimental conditions, for example the stringency of washing steps to remove weakly or non-specifically bound phage, can only be determined by trial and error based on the final outcome of the experiment. Finally, even though pIII and to a lesser extent the other proteins of the phage coat are generally tolerant to the fusion of heterologous polypeptides, the need to be incorporated into the phage biogenesis process imposes biological constraints that can limit library diversity. Therefore, there is a great need in the art for techniques capable of overcoming these limitations.

Protein libraries have also been displayed on the surface of bacteria, fungi, or higher cells. Cell displayed libraries are typically screened by flow cytometry (Georgiou et al. 1997, Daugherty et al. 2000). However, just as in phage display, the protein has to be engineered for expression on the outer cell surface. This imposes several potential limitations. For example, the requirement for display of the protein on the surface of a cell imposes biological constraints that limit the diversity of the proteins and protein mutants that can be screened. Also, complex proteins consisting of several polypeptide chains cannot be readily displayed on the surface of bacteria, filamentous phages or yeast. As such, there is a great need in the art for technology which circumvents all the above limitations and provides an entirety novel means for the screening of very large polypeptide libraries.

The use of techniques allowing creation of antibodies with improved affinities to anthrax antigens in particular is needed. Anthrax (*B. anthracis*) is a zoonotic soil organism endemic to many parts of the world. Infection through the inhalation of the heat resistant spores of the Gram positive bacterium, *B. anthracis*, results in up to 80% mortality rate if left untreated (Shafazand, 1999). In fact, *B. anthracis* was one of the first biological warfare agents to be developed and continues to be perceived as a major threat. While vaccine strains have been developed, widespread use is neither available nor recommended by the CDC.

Following inhalation, the *B. anthracis* spores germinate in the alveolar macrophages and migrate to lymph nodes where they multiply and enter the bloodstream, quickly reaching $10^7$-$10^8$ organisms per milliliter of blood (Dixon et al., 1999). The vegetative bacteria excrete a tripartite exotoxin that is responsible for the etiology of the disease. The toxin is an 83 kDa polypeptide, protective antigen (PA), that binds to a recently identified receptor on the surface of macrophages (Bradley et al., 2001). Identification of improved antibodies specific for anthrax antigens would offer the potential for new and improved therapeutic and diagnostic regimens and thus represent an important advance.

SUMMARY OF THE INVENTION

In one aspect, the invention provides an isolated antibody or fragment thereof that binds immunologically to *Bacillus anthracis* protective antigen with an affinity Kd of between about 140 pM and about 21 pM as determined by surface plasmon resonance. Such an antibody or fragment thereof may be further defined as binding immunologically to *Bacillus anthracis* protective antigen with a binding affinity Kd of between about 96 pM and about 21 pM and/or between about 35 pM and about 21 pM. The isolated antibody or fragment thereof may still further be defined as comprising an Fc domain of IgA, IgD, IgE, IgG or IgM. The antibody may be a humanized antibody and may be a human antibody. In certain embodiments, the isolated antibody or fragment thereof comprises an scFv fragment and antibody constant regions forming a monovalent antibody portion of at least 40 kDa.

In another aspect, the invention provides an isolated antibody or fragment thereof that binds immunologically to *Bacillus anthracis* protective antigen and comprises the variable light and variable heavy chain of SEQ ID NO:21, with the exception that the variable light and variable heavy chain comprise a modification selected from the group consisting of: I21V, S22G, L33S, Q38R, L46F, Q55L, S56P, T74A, S76N, Q78L, L94P, S7P, K19R, S30N, T57S, K62R, K64E, T68I, and M80L; wherein said I21V, S22G, L33S, Q38R, L46F, Q55L, S56P, T74A, S76N, Q78L and L94P are in the variable light chain and wherein said S7P, K19R, S30N, T57S, K62R, K64E, T68I and M80L are in the variable heavy chain. In certain embodiments of the invention, the isolated antibody or fragment thereof may be defined as comprising from about two to at all of said modifications, including about 3, 4, 5, 6, 7, 8, 9, 10, 11, 12, 13, 14, 15, 16, 17, 18 or all of the modifications, including all possible combinations of the foregoing modifications.

In certain aspects of the invention, the isolated antibody or fragment thereof is further defined as binding immunologically to *Bacillus anthracis* protective antigen with an affinity Kd of between about 140 pM and about 21 pM as determined by surface plasmon resonance. In further embodiments of the invention the antibody or fragment thereof comprises Q55L and S56P. The isolated antibody or fragment thereof may comprising the variable light and/or variable heavy chain of SEQ ID NO:22 or SEQ ID NO:24. In one embodiment, the isolated antibody or fragment thereof comprises SEQ ID NO:22 and/or SEQ ID NO:24. The isolated antibody or fragment thereof may be further defined as a scAb, Fab or SFv and may also be further defined as comprising an Fc domain of IgA, IgD, IgE, IgG or IgM. The isolated antibody or fragment thereof may be a humanized antibody and may be human. In particular embodiments, the isolated antibody or fragment thereof comprises an scFv fragment and antibody constant regions forming a monovalent antibody portion of at least 40 kDa.

In yet another aspect, the invention provides an isolated nucleic acid encoding an antibody or fragment thereof provided by the invention. In one embodiment, the nucleic acid encodes the variable light chain of SEQ ID NO:23 and/or SEQ ID NO:25. In another embodiment, the nucleic acid encodes the variable heavy chain of SEQ ID NO:23 and/or SEQ ID NO:25. In yet another embodiment, nucleic acid encodes the polypeptide of SEQ ID NO:23 and, in another embodiment, the polypeptide of SEQ ID NO:25.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2: Examples of targets visualized by APEx. (A) Fluorescence distribution of ABLEC™ cells expressing PA specific (14B7) and digoxigenin specific (Dig) scFv and labeled with 200 nM Bodipy™ conjugated fluorescent antigens. Histograms represent the mean fluorescence intensity of 10,000 *E. coli* events. (B) Histograms of cells expressing 14B7 or Dig scFv labeled with 200 nM of the 240kDa digoxigenin-phycoerythrin conjugate.

FIG. 3: Analysis of anti-PA antibody fragments selected using APEx (A) Signal Plasmon Resonance (SPR) analysis of anti-PA scAb binding to PA. (B) Table of affinity data acquired by SPR. (C) FC Histogram of anti-PA scFv in pAPEx1 expressed in *E. coli* and labeled with 200 nM PA-Bodipy™ conjugate as compared with anti-methamphetamine (Meth) scFv negative control.

FIG. 4: N-Terminal vs. C-Terminal anchoring strategy comparison. (A) Anti-digoxigenin Dig scfv, anti-PA M18 scFv and anti-methamphetamine Meth scFv expressed as N-terminal fusions in the pAPEx1 vector in *E. coli* specifically label with 200 nM of their respective antigen. (B) C-terminal fusions of same scFv in pAK200 vector specifically labeled with 200nM of their respective antigen.

DESCRIPTION OF ILLUSTRATIVE EMBODIMENTS

Figure 1A:
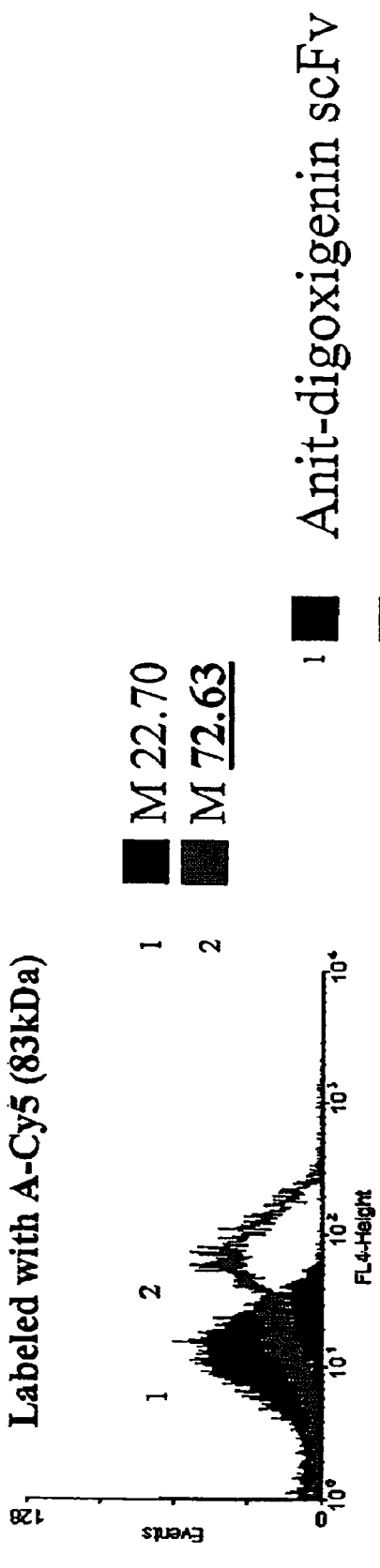
FIGS. 1A-B: Detection of ScFvs for Larger Target Antigen conjugated fluorophores.

The invention overcomes the limitations of the prior art by providing improved antibodies created using a novel method for isolating binding polypeptides. In the technique used, a library of polypeptide (e.g., antibody or other binding polypeptides) mutants can be constructed and expressed in Gram negative bacteria. The mutant polypeptides can be expressed as fusion proteins that are anchored on the inner (cytoplasmic) membrane of the bacterium facing the periplasm.

The antibodies isolated bind immunologically to Bacillus anthracis protective antigen with a 120 fold improvement in affinity over the starting antibody. The antibodies have important clinical and diagnostic applications. Infections due to Bacillus anthracis, commonly referred to as anthrax, most commonly occur in hoofed mammals, but serious forms of human anthrax include inhalation anthrax, cutaneous anthrax, and intestinal anthrax. Inhalation anthrax is usually fatal. The intestinal disease form of anthrax may follow the consumption of contaminated food and is characterized by an acute inflammation of the intestinal tract. Direct person-to-person spread of anthrax is extremely unlikely, if it occurs at all. Therefore, the CDC explains that there is no need to immunize or treat contacts of persons ill with anthrax, such as household contacts, friends, or co-workers, unless they also were also exposed to the same source of the infection.

For persons infected with anthrax, treatment success is limited by several factors, such as the increased incidence of antibiotic resistance and treatment delays that lessen the chance of survival. It is known that early treatment of anthrax with antibiotics is essential to reduce mortality—delays in treatment profoundly decrease survival rates. Early treatment, however, is difficult because initial symptoms of the infection, e.g., when the bacterial spores are inhaled, heretofore known as inhalation anthrax, may resemble those of the common cold. In addition, symptoms of anthrax infection, depending on how the bacterium is contracted, may take seven to sixty days to appear.

The pathogenicity of B. anthracis is expressed in two ways: a toxic effect made evident by the appearance of an edema, and a so-called lethal toxic effect that may lead to the death of the subject infected. These effects are attributed to the presence of toxins produced by a combination of three protein factors present in B. anthracis. In both humans and mammals, toxins will increase in the body even during early stages of infection when the host appears asymptomatic. This explains why delays in treatment can be fatal. Thus, there is not only a critical need for better anthrax intervention therapies, but a critical need for point-of-care, rapid, and extremely sensitive diagnostic tests to establish the presence of anthrax early in the infection.

Passive immunization in an effort to neutralize toxins with antibodies, usually polyclonal antibodies, has been used as a therapeutic intervention for a variety of bacterial infections (Keller and Stiehm, 2000). A major limitation of using polyclonal antisera in patients is the possibility of "serum sickness" due to a patient's immune response to proteins derived from a different species. In addition, higher affinity antibodies are more effective for toxin neutralization, but there is no general way to enhance intentionally the affinity of polyclonal sera or even monoclonal antibodies derived from hybridomas.

I. Antibodies and Use Thereof

The identification of high affinity engineered antibodies is an important advance. In accordance with the invention, an antibody includes any portion or fragment of an antibody, e.g., an scFv fragment. The antibody may be of any antibody class. The antibody may be, e.g., derived from an scFv fragment which further includes antibody constant regions to create monovalent antibody portion of, e.g., at least 40 kDa. The antibody may be affinity matured by selecting for clones having higher affinity than the wild-type antibody sequence cloned from a hybridoma after imperfect PCR amplification, e.g., error-prone expression libraries.

In one embodiment, an isolated antibody or fragment thereof may bind immunologically to Bacillus anthracis protective antigen with an affinity Kd of between about 140 pM and about 21 pM as determined by surface plasmon resonance. Such an antibody or fragment thereof may be further defined as binding immunologically to Bacillus anthracis protective antigen with a binding affinity Kd of between about 96 pM and about 21 pM and/or between about 35 pM and about 21 pM.

Affinity matured antibodies or portions thereof may be fused to create divalent homodimeric antibodies. The antibody or portions thereof may generally confer protection to a host against Bacillus anthracis toxin. The host may be, e.g., a human and exhibit, in one example, about a one-to-one stoichiometry. The present invention therefore includes a method of treating a host having or at risk of infection by Bacillus anthracis, the method comprising the step of administering to a host a composition comprising an antibody or fragment thereof provided by the invention. The composition may be administered after onset of symptoms or may be administered prophylactically. The antibodies of the invention may also find diagnostic use, for example, to detect exposure to anthrax.

II. Anchored Periplasmic Expression

Prior art methods of both phage display and bacterial cell surface display suffer from a limitation in that the protein is required, by definition, to be physically. displayed on the outer surface of the vehicle used, to allow unlimited access to the targets (immobilized for phage or fluorescently conjugated ligands for flow cytometry) (U.S. Pat. No. 5,223,409, the disclosure of which is specifically incorporated herein by reference in its entirety). However, certain proteins are known to be poorly displayed on phage (Maenaka et al., 1996; Corey et al., 1993) and the toxic effects of outer cell surface display have been treated at length (Daugherty et al., 1999). Further, there is no lipopolysaccharide to interfere with binding on the inner membrane.

Herein, the inventors have isolated improved antibodies using a technique in which binding proteins can be expressed on the periplasmic face of the inner membrane as fusion proteins yet still be accessible to relatively large ligands. As used herein, the term "binding polypeptide" includes not only antibodies, but also fragments of antibodies, as well as any other peptides, including proteins potentially capable of binding a given target molecule. The antibody or other binding peptides may be expressed with the invention as fusion polypeptides with polypeptides capable of serving as anchors to the periplasmic face of the inner membrane. Such a technique may be termed "Anchored Periplasmic Expression" or "APEx".

The periplasmic compartment is contained between the inner and outer membranes of Gram negative cells. As a sub-cellular compartment, it is subject to variations in size, shape and content that accompany the growth and division of the cell. Within a framework of peptidoglycan heteropolymer is a dense mileau of periplasmic proteins and little water, lending a gel-like consistency to the compartment (Hobot et al., 1984; van Wielink and Duine, 1990). The peptidoglycan is polymerized to different extents depending on the proximity to the outer membrane, close-up it forms the murein sacculus that affords cell shape and resistance to osmotic lysis.

The outer membrane (see Nikaido, 1996) is composed of phospholipids, porin proteins and, extending into the medium, lipopolysaccharide (LPS). The molecular basis of outer membrane integrity resides with LPS ability to bind divalent cations ($Mg^{2+}$ and $Ca^{2+}$) and link each other electrostatically to form a highly ordered quasi-crystalline ordered "tiled roof" on the surface (Labischinski et al., 1985). The membrane forms a very strict permeability barrier allowing passage of molecules no greater than around 650 Da (Burman et al., 1972; Decad and Nikaido, 1976) via the porins. The large water filled porin channels are primarily responsible for allowing free passage of mono and disaccharides, ions and amino acids in to the periplasm compartment (Nakae, 1976; Nikaido and Nakae, 1979; Nikaido and Vaara, 1985). With such strict physiological regulation of access by molecules to the periplasm it may appear, at first glance, inconceivable that APEx should work unless the ligands employed are at or below the 650 Da exclusion limit or are analogues of normally permeant compounds. However, the inventors have shown that ligands greater than 2000 Da in size can diffuse into the periplasm without disruption of the periplasmic membrane. Such diffusion can be aided by one or more treatments of a bacterial cell, thereby rendering the outer membrane more permeable, as is described herein below.

III. Screening Candidate Molecules

The present inventors employed techniques for identifying molecules capable of binding a target ligand. The binding polypeptides screened may comprise large libraries of diverse candidate substances, or, alternatively, may comprise particular classes of compounds selected with an eye towards structural attributes that are believed to make them more likely to bind the target ligand. In one embodiment of the invention, the candidate binding protein is an antibody, or a fragment or portion thereof. In other embodiments of the invention, the candidate molecule may be another binding protein.

To identify a candidate molecule capable of binding a target ligand, one may carry out the steps of: providing a population of Gram negative bacterial cells comprising fusion proteins between candidate binding polypeptides and a sequence anchored to the periplasmic face of the inner membrane; admixing the bacteria and at least a first labeled target ligand capable of contacting the candidate binding polypeptide and identifying at least a first bacterium expressing a molecule capable of binding the target ligand.

In the aforementioned method, the binding between the anchored candidate binding protein and the labeled ligand will prevent diffusing out of the cell. In this way, molecules of the labeled ligand can be retained in the periplasm of the bacterium. Alternatively, the periplasm can be removed, whereby the anchoring will cause retention of the bound candidate molecule. The labeling may then be used to isolate the cell expressing a binding polypeptide capable of binding the target ligand, and in this way, the gene encoding the binding polypeptide isolated. The molecule capable of binding the target ligand may then be produced in large quantities using in vivo or ex vivo expression methods, and then used for any desired application, for example, for diagnostic or therapeutic applications, as described below.

As used herein the term "candidate molecule" or "candidate polypeptide" refers to any molecule or polypeptide that may potentially have affinity for a target ligand. The candidate substance may be a protein or fragment thereof, including a small molecule such as synthetic molecule. The candidate molecule may in one embodiment of the invention, comprise an antibody sequence or fragment thereof. Such sequences may be particularly designed for the likelihood that they will bind a target ligand.

Binding polypeptides or antibodies isolated in accordance with the invention also may help ascertain the structure of a target ligand. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen. On the other hand, one may simply acquire, from various commercial sources, small molecule libraries that are believed to meet the basic criteria for binding the target ligand. Such libraries could be provided by way of nucleic acids encoding the small molecules or bacteria expressing the molecules.

A. Cloning of Binding Protein Coding Sequences

The binding affinity of an antibody or other binding protein can, for example, be determined by the Scatchard analysis of Munson & Pollard (1980). After a bacterial cell is identified that produces molecules of the desired specificity, affinity, and/or activity, the corresponding coding sequence may be cloned. In this manner, DNA encoding the molecule can be isolated and sequenced using conventional procedures (e.g., by using oligonucleotide probes that are capable of binding specifically to genes encoding the antibody or binding protein).

Once isolated, the antibody or binding protein DNA may be placed into expression vectors, which can then transfected into host cells such as simian COS cells, Chinese hamster ovary (CHO) cells, or myeloma cells that do not otherwise produce immunoglobulin protein, to obtain the synthesis of binding protein in the recombinant host cells. The DNA also may be modified, for example, by substituting the coding sequence for human heavy and light chain constant domains in place of the homologous murine sequences (Morrison, et al., 1984), or by covalently joining to the immunoglobulin coding sequence all or part of the coding sequence for a non-immunoglobulin polypeptide. In that manner, "chimeric" or "hybrid" binding proteins are prepared that have the desired binding specificity.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for the target ligand and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

It will be understood by those of skill in the art that nucleic acids may be cloned from viable or inviable cells. In the case of inviable cells, for example, it may be desired to use amplification of the cloned DNA, for example, using PCR. This may also be carried out using viable cells either with or without further growth of cells.

B. Maximization of Protein Affinity for Ligands

In a natural immune response, antibody genes accumulate mutations at a high rate (somatic hypermutation). Some of the changes introduced will confer higher affinity, and B cells displaying high-affinity surface immunoglobulin. This natural process can be mimicked by employing the technique known as "chain shuffling" (Marks et al., 1992). In this method, the affinity of "primary" human antibodies obtained in accordance with the invention could be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large antibody repertoires was described by Waterhouse et al., (1993), and the isolation of a high affinity human antibody directly from such large phage library was reported by Griffith et al., (1994). Gene shuffling also can be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by the phage display technique is replaced with a repertoire of human V domain genes, creating rodent-human chimeras. Selection of the antigen results in isolation of human variable regions capable of restoring a functional antigen-binding site, i.e. the epitope governs (imprints) the choice of partner. When the process is repeated in order to replace the remaining rodent V domain, a human antibody is obtained (see PCT patent application WO 93/06213, published Apr. 1, 1993). Unlike traditional humanization of rodent antibodies by CDR grafting, this technique provides completely human antibodies, which have no framework or CDR residues of rodent origin.

C. Labeled Ligands

In one embodiment of the invention, an antibody or binding protein is isolated which has affinity for a labeled ligand. By permeabilization and/or removal of the periplasmic membrane of a Gram negative bacterium in accordance with the invention, labeled ligands of potentially any size could be screened. In the absence of removal of the periplasmic membrane, it will typically be preferable that the labeled ligand is less that 50,000 Da in size in order to allow efficient diffusion of the ligand across the bacterial periplasmic membrane.

As indicated above, it will typically be desired in accordance with the invention to provide a ligand which has been labeled with one or more detectable agent(s). This can be carried out, for example, by linking the ligand to at least one detectable agent to form a conjugate. For example, it is conventional to link or covalently bind or complex at least one detectable molecule or moiety. A "label" or "detectable label" is a compound and/or element that can be detected due to specific functional properties, and/or chemical characteristics, the use of which allows the ligand to which it is attached to be detected, and/or further quantified if desired. Examples of labels which could be used with the invention include, but are not limited to, enzymes, radiolabels, haptens, fluorescent labels, phosphorescent molecules, chemiluminescent molecules, chromophores, luminescent molecules, photoaffinity molecules, colored particles or ligands, such as biotin.

In one embodiment of the invention, a visually-detectable marker is used such that automated screening of cells for the label can be carried out. In particular, fluorescent labels are beneficial in that they allow use of flow cytometry for isolation of cells expressing a desired binding protein or antibody. Examples of agents that may be detected by visualization with an appropriate instrument are known in the art, as are methods for their attachment to a desired ligand (see, e.g., U.S. Pat. Nos. 5,021,236; 4,938,948; and 4,472,509, each incorporated herein by reference). Such agents can include paramagnetic ions; radioactive isotopes; fluorochromes; NMR-detectable substances and substances for X-ray imaging. Types of fluorescent labels that may be used with the invention will be well known to those of skill in the art and include, for example, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Magnetic screening techniques are well known to those of skill in the art (see, for example, U.S. Pat. Nos. 4,988,618, 5,567,326 and 5,779,907). Examples of paramagnetic ions that could be used as labels in accordance with such techniques include ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III). Ions useful in other contexts include but are not limited to lanthanum (III), gold (III), lead (II), and especially bismuth (III).

Another type of ligand conjugate contemplated in the present invention are those where the ligand is linked to a secondary binding molecule and/or to an enzyme (an enzyme tag) that will generate a colored product upon contact with a chromogenic substrate. Examples of such enzymes include urease, alkaline phosphatase, (horseradish) hydrogen peroxidase or glucose oxidase. In such instances, it will be desired that cells selected remain viable. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Molecules containing azido groups also may be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide-binding proteins in crude cell extracts (Owens & Haley, 1987; Atherton et al., 1985). The 2- and 8-azido nucleotides have also been used to map nucleotide-binding domains of purified proteins (Khatoon et al., 1989; King et al., 1989; and Dholakia et al., 1989) and may be used as ligand binding agents.

Labeling can be carried out by any of the techniques well known to those of skill in the art. For instance, ligands can be labeled by contacting the ligand with the desired label and a chemical oxidizing agent such as sodium hypochlorite, or an enzymatic oxidizing agent, such as lactoperoxidase. Similarly, a ligand exchange process could be used. Alternatively, direct labeling techniques may be used, e.g., by incubating the label, a reducing agent such as $SNCl_2$, a buffer solution such as sodium-potassium phthalate solution, and the ligand. Intermediary functional groups on the ligand could also be used, for example, to bind labels to a ligand in the presence of diethylenetriaminepentaacetic acid (DTPA) or ethylene diaminetetracetic acid (EDTA).

Other methods are also known in the art for the attachment or conjugation of a ligand to its conjugate moiety. Some attachment methods involve the use of an organic chelating agent such as diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the ligand (U.S. Pat. Nos. 4,472,509 and 4,938,948, each incorporated herein by reference). Ligands also may be reacted with an enzyme in the presence of a coupling agent such as glutaraldehyde or periodate. Conjugates with fluorescein markers can be prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

The ability to specifically label periplasmic expressed proteins with appropriate fluorescent ligands also has applications other than library screening. Specifically labeling with fluorescent ligands and flow cytometry can be used for monitoring production during protein manufacturing. While flow cytometry has been used previously for the analysis of bacterial cells, it has not been used for the specific labeling and quantitation of periplasmic proteins. However, a large number of commercially important proteins including IGF-1 several interleukins, enzymes such as urokinase-type plasminogen activator, antibody fragments, inhibitors (e.g., Bovine pancreatic trypsin inhibitor) are expressed in recombinant bacteria in a form secreted into the periplasmic space. The level of production of such proteins within each cell in a culture can be monitored by utilizing an appropriate fluorescent ligand and flow cytometric analysis, according to the techniques taught by the present invention.

Generally, monitoring protein expression requires cell lysis and detection of the protein by immunological techniques or following chromatographic separation. However, ELISA or western blot analysis is time-consuming and does not provide information on the distribution of expression among a cell population and cannot be used for on-line monitoring (Thorstenson et al., 1997; Berrier et al., 2000). In contrast, FACS labeling is rapid and simple and can well be applied to online monitoring of industrial size fermentations of recombinant proteins expressed in Gram-negative bacteria. Similarly, the invention could be used to monitor the production of a particular byproduct of a biological reaction. This also could be used to measure the relative concentration or specific activity of an enzyme expressed in vivo in a bacterium or provided ex vivo.

Once a ligand-binding protein, such as an antibody, has been isolated in accordance with the invention, it may be desired to link the molecule to at least one agent to form a conjugate to enhance the utility of that molecule. For example, in order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety which may be detected using an assay. Techniques for labeling such a molecule are known to those of skill in the art and have been described herein above.

Labeled binding proteins such as antibodies which have been prepared in accordance with the invention may also then be employed, for example, in immunodetection methods for binding, purifying, removing, quantifying and/or otherwise generally detecting biological components such as protein(s), polypeptide(s) or peptide(s). Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev (1999); Gulbis and Galand (1993); De Jager et al. (1993), each incorporated herein by reference. Such techniques include binding assays such as the various types of enzyme linked immunosorbent assays (ELISAs) and/or radioimmunoassays (RIA) known in the art.

The ligand-binding molecules, including antibodies, prepared in accordance with the present invention may also, for example, in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Abbondanzo et al., 1990).

IV. Automated Screening with Flow Cytometry

Fluorescence activated cell sorting (FACS) screening or other automated flow cytometric techniques may be used for the efficient isolation of a bacterial cell comprising a labeled ligand bound to a candidate molecule and linked to the outer face of the cytoplasmic membrane of the bacteria. Instruments for carrying out flow cytometry are known to those of skill in the art and are commercially available to the public. Examples of such instruments include FACS Star Plus, FACScan and FACSort instruments from Becton Dickinson (Foster City, Calif.) Epics C from Coulter Epics Division (Hialeah, Fla.) and MoFlo from Cytomation (Colorado Springs, Colo.).

Flow cytometric techniques in general involve the separation of cells or other particles in a liquid sample. Typically, the purpose of flow cytometry is to analyze the separated particles for one or more characteristics thereof, for example, presence of a labeled ligand or other molecule. The basis steps of flow cytometry involve the direction of a fluid sample through an apparatus such that a liquid stream passes through a sensing region. The particles should pass one at a time by the sensor and are categorized base on size, refraction, light scattering, opacity, roughness, shape, fluorescence, etc.

Rapid quantitative analysis of cells proves useful in biomedical research and medicine. Apparati permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of the interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls. Analysis of the class of cells is very important, as high detection performance may be expected only if an appropriate characteristic of the cells is obtained.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent-tagged antibodies, which are used to mark one or more cell types for separation.

Other examples of methods for flow cytometry that could include, but are not limited to, those described in U.S. Pat. Nos. 4,284,412; 4,989,977; 4,498,766; 5,478,722; 4,857,451; 4,774,189; 4,767,206; 4,714,682; 5,160,974; and 4,661,913, each of the disclosures of which are specifically incorporated herein by reference.

For the present invention, an important aspect of flow cytometry is that multiple rounds of screening can be carried out sequentially. Cells may be isolated from an initial round of sorting and immediately reintroduced into the flow cytometer and screened again to improve the stringency of the screen. Another advantage known to those of skill in the art is that nonviable cells can be recovered using flow cytometry. Since flow cytometry is essentially a particle sorting technology, the ability of a cell to grow or propagate is not necessary. Techniques for the recovery of nucleic acids from such nonviable cells are well known in the art and may include, for example, use of template-dependent amplification techniques including PCR.

V. Nucleic Acid-Based Expression Systems

Nucleic acid-based expression systems may find use, in certain embodiments of the invention, for the expression of recombinant proteins. For example, one embodiment of the invention involves transformation of Gram negative bacteria with the coding sequences of fusion polypeptides comprising a candidate antibody or other binding protein having affinity for a selected ligand and the expression of such molecules on the cytoplasmic membrane of the Gram negative bacteria. In other embodiments of the invention, expression of such coding sequences may be carried, for example, in eukaryotic host cells for the preparation of isolated binding proteins having specificity for the target ligand. The isolated protein could then be used in one or more therapeutic or diagnostic applications.

A. Methods of Nucleic Acid Delivery

Certain aspects of the invention may comprise delivery of nucleic acids to target cells. For example, bacterial host cells may be transformed with nucleic acids encoding candidate molecules potentially capable of binding a target ligand, In particular embodiments of the invention, it may be desired to target the expression to the cytoplasmic membrane of the bacteria. Transformation of eukaryotic host cells may similarly find use in the expression of various candidate molecules identified as capable of binding a target ligand.

Suitable methods for nucleic acid delivery for transformation of a cell are believed to include virtually any method by which a nucleic acid (e.g., DNA) can be introduced into such a cell, or even an organelle thereof. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466. and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

1. Electroporation

In certain embodiments of the present invention, a nucleic acid is introduced into a cell via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

2. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

B. Vectors

Vectors may find use with the current invention, for example, in the transformation of a Gram negative bacterium with a nucleic acid sequence encoding a candidate polypeptide which one wishes to screen for ability to bind a target ligand. In one embodiment of the invention, an entire heterogeneous "library" of nucleic acid sequences encoding target polypeptides may be introduced into a population of bacteria, thereby allowing screening of the entire library. The term "vector" is used to refer to a carrier nucleic acid molecule into which a nucleic acid sequence can be inserted for introduction into a cell where it can be replicated. A nucleic acid sequence can be "exogenous," or "heterologous", which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art may construct a vector through standard recombinant techniques, which are described in Maniatis et al., 1988 and Ausubel et al., 1994, both of which references are incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. One example of such promoter that may be used with the invention is the *E. coli* arabinose promoter. Those of skill in the art of molecular biology generally are familiar with the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Termination Signals

The vectors or constructs prepared in accordance with the present invention will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels.

Terminators contemplated for use in the invention include any known terminator of transcription described herein or known to one of ordinary skill in the art, including but not limited to, for example, rhp dependent or rho independent terminators. In certain embodiments, the termination signal may be a lack of transcribable or translatable sequence, such as due to a sequence truncation.

5. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

6. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

C. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In particular embodiments of the invention, a host cell is a Gram negative bacterial cell. These bacteria are suited for use with the invention in that they posses a periplasmic space between the inner and outer membrane and, particularly, the aforementioned inner membrane between the periplasm and cytoplasm, which is also known as the cytoplasmic membrane. As such, any other cell with such a periplasmic space could be used in accordance with the invention. Examples of Gram negative bacteria that may find use with the invention may include, but are not limited to, *E. coli, Pseudomonas aeruginosa, Vibrio cholera, Salmonella typhimurium, Shigella flexneri, Haemophilus influenza, Bordotella pertussi, Erwinia amylovora, Rhizobium* sp. The Gram negative bacterial cell may be still further defined as bacterial cell which has been transformed with the coding sequence of a fusion polypeptide comprising a candidate binding polypeptide capable of binding a selected ligand. The polypeptide is anchored to the outer face of the cytoplasmic membrane, facing the periplasmic space, and may comprise an antibody coding sequence or another sequence. One means for expression of the polypeptide is by attaching a leader sequence to the polypeptide capable of causing such directing.

Numerous prokaryotic cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5/α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for bacteriophage.

Many host cells from various cell types and organisms are available and would be known to one of skill in the art. Similarly, a viral vector may be used in conjunction with a prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

D. Expression Systems

Numerous expression systems exist that comprise at least a part or all of the compositions discussed above. Such systems could be used, for example, for the production of a polypeptide product identified in accordance with the invention as capable of binding a particular ligand. Prokaryote-based systems can be employed for use with the present invention to produce nucleic acid sequences, or their cognate polypeptides, proteins and peptides. Many such systems are commercially and widely available. Other examples of expression systems comprise of vectors containing a strong prokaryotic promoter such as T7, Tac, Trc, BAD, lambda pL, Tetracycline or Lac promoters, the pET Expression System and an *E. coli* expression system.

E. Candidate Binding Proteins and Antibodies

In certain aspects of the invention, candidate antibodies or other recombinant polypeptides, including proteins and short peptides potentially capable of binding a target ligand are expressed on the cytoplasmic membrane of a host bacterial cell. By expression of a heterogeneous population of such antibodies or other binding polypeptides, those antibodies having a high affinity for a target ligand may be identified. The identified antibodies may then be used in various diagnostic or therapeutic applications, as described herein.

As used herein, the term "antibody" is intended to refer broadly to any immunologic binding agent such as IgG, IgM, IgA, IgD and IgE. The term "antibody" is also used to refer to any antibody-like molecule that has an antigen binding region, and includes antibody fragments such as Fab', Fab, F(ab')$_2$, single domain antibodies (DABs), Fv, scFv (single chain Fv), and engineering multivalent antibody fragments such as dibodies, tribodies and multibodies. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Once an antibody having affinity for a target ligand is identified, the antibody or ligand binding polypeptide may be purified, if desired, using filtration, centrifugation and various chromatographic methods such as HPLC or affinity chromatography. Fragments of such polypeptides, including antibodies, can be obtained from the antibodies so produced by methods which include digestion with enzymes, such as pepsin or papain, and/or by cleavage of disulfide bonds by chemical reduction. Alternatively, antibody or other polypeptides, including protein fragments, encompassed by the present invention can be synthesized using an automated peptide synthesizer.

A molecular cloning approach comprises one suitable method for the generation of a heterogeneous population of candidate antibodies that may then be screened in accordance with the invention for affinity to target ligands. In one embodiment of the invention, combinatorial immunoglobulin phagemid can be prepared from RNA isolated from the spleen of an animal. By immunizing an animal with the ligand to be screened, the assay may be targeted to the particular antigen. The advantages of this approach over conventional techniques are that approximately $10^4$ times as many antibodies can be produced and screened in a single round, and that new specificities are generated by H and L chain combination which further increases the chance of finding appropriate antibodies.

VI. Manipulation and Detection of Nucleic Acids

In certain embodiments of the invention, it may be desired to employ one or more techniques for the manipulation, isolation and/or detection of nucleic acids. Such techniques may include, for example, the preparation of vectors for transformation of host cells as well as methods for cloning selected nucleic acid segments from a transgenic cell. Methodology for carrying out such manipulations will be well known to those of skill in the art in light of the instant disclosure.

Nucleic acids used as a template for amplification may be isolated from cells, tissues or other samples according to standard methodologies (Sambrook et al., 1989). In certain embodiments, analysis may be performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to a selected nucleic acid sequence are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated. radiolabel or fluorescent label or even via a system using electrical and/or thermal impulse signals (Affymax technology; Bellus, 1994).

A, number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) discloses a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Use of Anchored Periplasmic Expression to Isolate Antibodies With Over a 120-Fold Improvement in Affinity for the *Bacillus anthracis* Protective Antigen The screening of large libraries requires a physical link between a gene, the protein it encodes, and the desired function. Such a link can be established using a variety of in vivo display technologies that have proven invaluable for mechanistic studies, for biotechnological purposes and for proteomics research (Hoess, 2001; Hayhurst and Georgiou, 2001; Wittrup, 2000).

APEx is an alternative approach that allows screening by flow cytometry (FC). FC combines high throughput with real-time, quantitative, multi-parameter analysis of each library member. With sorting rates on the order of more than 400 million cells per hour, commercial FC machines can be employed to screen libraries of the size accessible within the constraints of microbial transformation efficiencies. Furthermore, multi-parameter FC can provide valuable information regarding the function of each and every clone in the library in real time, thus helping to guide the library construction process and optimize sorting conditions (Boder and Wittrup, 2000; Daugherty et al., 2000).

Bacterial and yeast protein display in combination with FC has been employed for the engineering of high affinity antibodies to a variety of ligands (Daugherty et al., 1999; Boder et al., 2000). However, the requirement for the display of proteins on cell surfaces imposes a number of biological constraints that can impact library screening applications. Processes such as the unfolded protein response in eucaryotes or the stringency of protein sorting to the outer membrane of Gram-negative bacteria limit the diversity of the polypeptides that are actually compatible with surface display (Sagt et al., 2002; Sathopoulos et al., 1996). In addition, microbial surfaces are chemically complex structures whose macromolecular composition can interfere with protein:ligand recognition. This problem is particularly manifest in Gram-negative bacteria because the presence of lipopolysaccharides on the outer membrane presents a steric barrier to protein:ligand recognition, a fact that likely contributed to the evolution of specialized appendages, such as pili or fimbriae (Hultgren et al., 1996).

APEx overcomes the biological constraints and antigen access limitations of previous display strategies, enabling the efficient isolation of antibodies to virtually any size antigen. In APEx, proteins are tethered to the external (periplasmic) side of the *E. coli* cytoplasmic membrane as either N- or C-terminal fusions, thus eliminating biological constraints associated with the display of proteins on the cell surface. Following chemical/enzymatic permeabilization of the bacterial outer membrane, *E. coli* cells expressing anchored scFv antibodies can be specifically labeled with fluorescent antigens, of at least 240 kDa,. and analyzed by FC. By using APEx the inventors have demonstrated the efficient isolation of antibodies with markedly improved ligand affinities, including an antibody fragment to the protective antigen of *Bacillus anthracis* with an affinity that was increased over 120-fold.

A. Anchored Periplasmic Expression and Detection of Ligand Binding

For screening applications, an ideal expression system should minimize cell toxicity or growth abnormalities that can arise from the synthesis of heterologous polypeptides (Daugherty et al., 2000). Use of APEx avoids the complications that are associated with transmembrane protein fusions (Miroux and Walker, 1996; Mingarro et al., 1997). Unlike membrane proteins, bacterial lipoproteins are not known to require the SRP or YidC pathways for membrane anchoring (Samuelson et al., 2000). Lipoproteins are secreted across the membrane via the Sec pathway and once in the periplasm, a diacylglyceride group is attached through a thioether bond to a cysteine residue on the C-terminal side of the signal sequence. The signal peptide is then cleaved by signal peptidase II, the protein is fatty acylated at the modified cysteine residue, and finally the lipophilic fatty acid inserts into the membrane, thereby anchoring the protein (Pugsley, 1993; Seydel et al., 1999; Yajushi et al., 2000).

A sequence encoding the leader peptide and first six amino acids of the mature NlpA (containing the putative fatty acylation and inner membrane targeting sites) was employed for anchoring scFv antibodies to the periplasmic face of the inner membrane. NlpA is a non-essential *E. coli* lipoprotein that exclusively localizes to the inner membrane (Yu et al., 1986; Yamaguchi et al., 1988). Of particular note is the aspartate residue adjacent to the fatty acylated cysteine residue that is thought to be a consensus residue for inner membrane targeting (Yamaguchi et al., 1988). NlpA fusions to the 26-10 anti-digoxin/digoxigenin (Dig) scFv and to the anti-*B. anthracis* protective antigen (PA) 14B7 scFv were constructed and expressed from a lac promoter in *E. coli*. Following induction of the NlpA-[scFv] synthesis using IPTG, the cells were incubated with EDTA and lysozyme to disrupt the outer membrane and the cell wall. The permeabilized cells were mixed with the respective antigens conjugated to the fluorescent dye BODIPY™ (200 nM) and the cell fluorescence was determined by flow cytometry. Treated cells expressing the NlpA-[14B7 scFv] and the NlpA-[Dig scFv] exhibited an approximate 9-fold and 16-fold higher mean fluorescence intensity, respectively, compared to controls (FIG. 2A). Only background fluorescence was detected when the cells were mixed with unrelated fluorescent antigen, indicating negligible background binding under the conditions of the study.

To further evaluate the ability of antibody fragments anchored on the cytoplasmic membrane to bind bulky antigens, the inventors examined the ability of the NlpA-[Dig scFv] to recognize digoxigenin conjugated to the 240 kDa fluorescent protein phycoerythrin (PE). The conjugate was mixed with cells expressing NlpA-[Dig scFv] and treated with EDTA-lysozyme. A high cell fluorescence was observed indicating binding of digoxigenin-PE conjugate by the membrane anchored antibody (FIG. 2B). Overall, the accumulated data demonstrated that in cells treated with Tris-EDTA-lysozyme, scFvs anchored on the cytoplasmic membrane can readily bind to ligands ranging from small molecules to proteins of at least up to 240 kDa in molecular weight. Importantly, labeling with digoxigenin-PE followed by one round of flow cytometry resulted in an over 500-fold enrichment of bacteria expressing NlpA-[Dig scFv] from cells expressing a similar fusion with a scFv having unrelated antigen specificity.

B. Library Screening by APEx

A library of $1 \times 10^7$ members was constructed by error-prone PCR of the gene for the anti-PA 144B7 scFv and was fused to the NlpA membrane anchoring sequence. DNA sequencing of 12 library clones selected at random revealed an average of 2% nucleotide substitutions per gene. Following induction of NlpA-[14B7 mutant scFv] synthesis with IPTG, the cells were treated with Tris-EDTA-lysozyme, washed, and labeled with 200 nM PA-BODIPY™. Inner membrane integrity was monitored by staining with propidium iodide (PI). A total of $2 \times 10^8$ bacteria were sorted using an ultra-high throughput Cytomation Inc. MoFlo droplet deflection flow cytometer selectively gating for low PI fluorescence (630 nm emission) and high BODIPY™ fluorescence. Approximately 5% of the cells sorted with the highest 530 nm fluorescence (FL1) were collected, immediately restained with PI alone and resorted as above. Since no antigen was added during this second sorting cycle, only cells expressing antibodies that have slow dissociation kinetics remain fluorescent. The plating efficiency of this population was low, presumably due to a combination of potential scFv toxicity (Somerville et al., 1994; Hayhurst and Harris, 1999), Tris-EDTA-lysozyme treatment and exposure to the high shear flow cytometry environment. Therefore, to avoid loss of potentially high affinity clones, DNA encoding scFvs was rescued by PCR™ amplification of the approximately $1 \times 10^4$ fluorescent events recovered by sorting. It should be noted that the conditions used for PCR™ amplification result in the quantitative release of cellular DNA from the cells which have partially hydrolyzed cell walls due to the Tris-EDTA-lysozyme treatment during labeling. Following 30 rounds of PCR™ amplification, the DNA was ligated into pAPEx1 and transformed into fresh E. coli. A second round of sorting was performed exactly as above, except that in this case only the most fluorescent 2% of the population was collected and then immediately resorted to yield approximately 5,000 fluorescent events.

Figure 5:
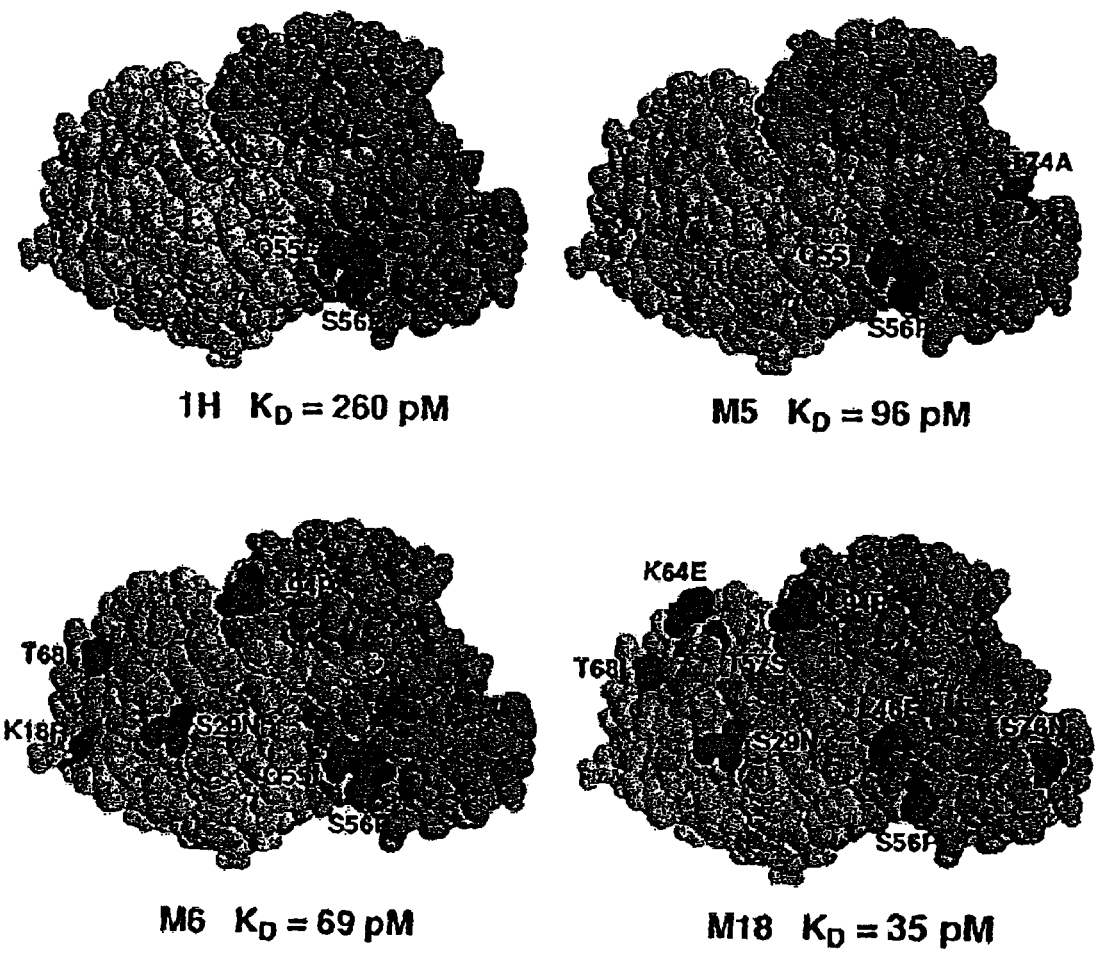
FIG. 5: View from the top of the antibody binding pocket showing the conformation and amino acid substitutions in the 1H, M5, M6 and M18 sequences.
Figure 6:
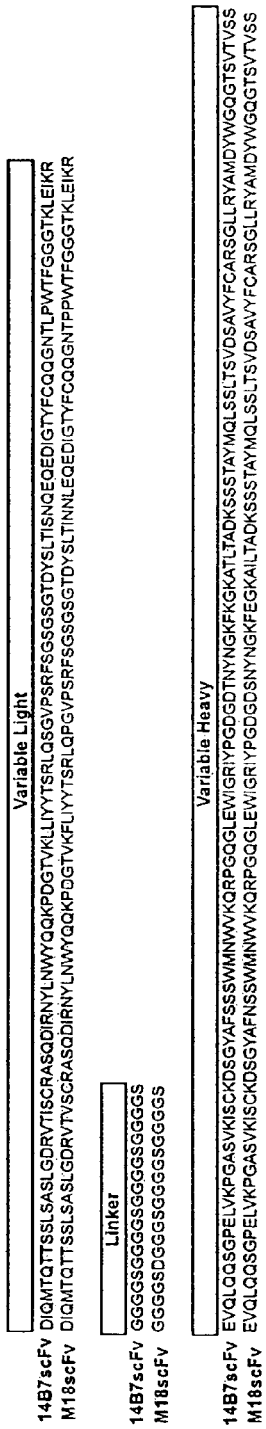
FIG. 6: Alignment of 14B7 scFv (SEQ ID NO:21) and M18 scFv (SEQ ID NO:23) sequences showing variable heavy and variable light chains and mutations made to improve binding affinity.

The scFv DNA from the second round was amplified by PCRT and ligated into pMoPac16 (Hayhurst et al., 2003) for expression of the antibody fragments in soluble form in the scAb format. A scAb antibody fragment is comprised of an scFv in which the light chain is fused to a human kappa constant region. This antibody fragment format exhibits better periplasmic solubility compared to scFvs (Maynard et al., 2002; Hayhurst, 2000). 20 clones in the scAb format were picked at random and grown in liquid cultures. Following induction with IPTG, periplasmic proteins were isolated and the scAb proteins were rank-ordered with respect to their relative antigen dissociation kinetics, using surface plasmon resonance (SPR) analysis. 11 of the 20 clones exhibited slower antigen dissociation kinetics compared to the 14B7 parental antibody. The 3 scAbs with the slowest antigen dissociation kinetics were produced in large scale and purified by Ni chromatography followed by gel filtration FPLC. Interestingly, all the library-selected clones exhibited excellent expression characteristics and resulted in yields of between 4-8 mg of purified protein per L in shake flask culture. Detailed BIACore analysis indicated that all 3 clones exhibit a substantially lower $K_D$ for PA compared to the parental 14B7 antibody (FIGS. 3A and 3B). The improved $K_D$ resulted primarily from slower antigen dissociation, (i.e. slower $k_{off}$). The highest affinity clone, M18, exhibited $K_D$ of 35 pM, with a $k_{off}$ of $4.2 \times 10^{-5}$ M$^{-1}$ sec$^{-1}$ which corresponds to a M18-PA half life of 6.6 hours. This represents over 120-fold affinity improvement compared to the parental antibody 14B7 ($K_D$=4.3 nM as determined by BIACore 3000). The mutations identified are given in FIG. 3B and a schematic showing the conformation of the 1H, M5, M6 and M18 antibodies is given in FIG. 5. The mutations for M5 were as follows: in the light chain, Q38R, Q55L, S56P, T74A, Q78L and in the heavy chain, K62R. For M6, the mutations were as follows: S22G, L33S, Q55L, S56P, Q78L AND L94 P, and in the heavy chain, S7P, K19R, S30N, T68I and M80L. For M18, the mutations were as follows: in the light chain, I21V, L46F, S56P, S76N, Q78L and L94P, and in the heavy chain, S30N, T57S, K64E and T68. FIG. 6 shows an alignment of 14B7 scFv (SEQ ID NO:21) and M18 scFv (SEQ ID NO:23) sequences indicating the variable heavy and variable light chains and mutations made. The nucleic acids encoding these sequences are given in SEQ ID NO:20 and SEQ ID NO:22, respectively.

The fluorescence intensity of Tris-EDTA-lysozyme permeabilized cells expressing NlpA fusions to the mutant antibodies varied in proportion to the antigen binding affinity. (FIG. 3C) For example, cells expressing the NlpA-[M18 scFv] protein displayed a mean fluorescence of 250 whereas the cells that expressed the parental 14B7 scFv exhibited a mean fluorescence of 30, compared to a background fluorescence of around 5 (FIG. 3B). Antibodies with intermediate affinities displayed intermediate fluorescence intensities in line with their relative affinity rank. The ability to resolve cells expressing antibodies exhibiting dissociation constants as low as 35 pM provides a reasonable explanation for why three unique very high affinity variants could be isolated and is indicative of the fine resolution that can be obtained with flow cytometric analysis.

The 3 clones analyzed in detail, M5, M6 and M18, contained 7, 12, and 11 amino acid substitutions, respectively. In earlier studies using phage display (Maynard et al., 2002; U.S. patent application Ser. No. 10/288,269, filed Nov. 5, 2002, the disclosure of which is incorporated herein by reference in the entirety), the inventors isolated a variant of the 14B7 scFv by three cycles, each consisting of 1) mutagenic error prone PCR™,2) five rounds of phage panning and 3) DNA shuffling of the post-panning clones. The best clone isolated in that study, 1H, contained Q55L and S56P substitutions and exhibited a $K_D$ of 150 pM (as determined by a BIACore3000). These two mutations likely increase the hydrophobicity of the binding pocket adding to the mounting evidence that an increase in hydrophobic interactions is a dominant effect in antibody affinity maturation (Li et al., 2003). The same amino acid substitutions are also found in the M5 and M6 clones isolated by APEx. However, the presence of the additional mutations in these two clones conferred a further increase in affinity. It is noteworthy that the M5, M6 and M18 were isolated following a single round of asexual PCR™ yet they all had higher affinity relative to the best antibody that could be isolated by phage display, even following multiple rounds of sexual mutagenesis and selection.

M18, the highest affinity clone isolated by APEx, contained the S56P mutation but lacked the Q55L substitution found in 1H, M5, and M6. When the QSSL substitution was introduced into M18 by site specific mutagenesis, the resultant ScAb exhibited a further improvement in antigen binding ($K_D$=21 pM) with a $k_{on}$ of $1.1 \times 10^6$ $M^{-1}$ $sec^{-1}$ and a $k_{off}$ of $2.4 \times 10^{-5}$ $sec^{-1}$, corresponding to a complex half life of 11.6 hours. However, the introduction of this mutation reduced the yield of purified protein more than 5-fold to 1.2 mg/L in shake flask culture. The modified M18 sequence is given in SEQ ID NO:25 and the nucleic acid encoding this sequence is given in SEQ ID NO:24.

C. APEx of Phage Displayed scFv Antibodies

Numerous antibody fragments to important therapeutic and diagnostic targets have been isolated from repertoire libraries screened by phage display. It is desirable to develop a means for rapid antigen binding analysis and affinity maturation of such antibodies without the need for time consuming subcloning steps. Antibodies are most commonly displayed on filamentous phage via fusion to the N-terminus of the phage gene 3 minor coat protein (g3p) (Barbas et al., 1991). During phage morphogenesis, g3p becomes transiently attached to the inner membrane via its extreme C-terminus, before it can be incorporated onto the growing virion (Boeke and Model, 1982). The antibody fragments are thus both anchored and displayed in the periplasmic compartment. Therefore, the inventors evaluated whether g3p fusion proteins can be exploited for antibody library screening purposes using the APEx format. The high affinity anti-PA M18 scFv discussed above, the anti-digoxin/digoxigenin 26-10 scFv, and an anti-methamphetamine scFv (Meth) were cloned in frame to the N-terminus of g3p downstream from a lac promoter in phagemid pAK200, which is widely used for phage display purposes and utilizes a short variant of gene III for g3p display (Krebber et al., 1997). Following induction with IPTG, cells expressing scFv-g3p fusions were permeabilized by Tris-EDTA-lysozyme and labeled with the respective fluorescent antigens (FIG. 4). High fluorescence was obtained for all three scFvs only when incubated with their respective antigens. Significantly, the mean fluorescence intensity of the scFvs fused to the N-terminus of g3p was comparable to that obtained by fusion to the C-terminus of the NlpA anchor. The results in FIG. 4 demonstrate that: (i) large soluble domains can be tethered N-terminally to a membrane anchor; (ii) antibody fragments cloned into phagemids for display on filamentous phage can be readily analyzed by flow cytometry using the APEx format, and (iii) scFv antibodies can be anchored on the cytoplasmic membrane either as N- or C-terminal fusions without loss of antigen binding.

Example 2

Discussion

The inventors have developed a allowing efficient selection of high affinity ligand-binding proteins, and particularly scFv antibodies, from combinatorial libraries. In one aspect, APEx is based on the anchoring of proteins to the outer side of the inner membrane, followed by disruption of the outer membrane prior to incubation with fluorescently labeled antigen and FC sorting. This strategy offers several advantages over previous bacterial periplasmic and surface display approaches: 1) by utilizing a fatty acylated anchor to retain the protein in the inner membrane, a fusion as short as 6 amino acids is all that was required for the successful display, potentially decreasing deleterious effects that larger fusions may impose; 2) the inner membrane lacks molecules such as LPS or other complex carbohydrates that can sterically interfere with large antigen binding to displayed antibody fragments; 3) the fusion must only traverse one membrane before it is displayed; 4) both N- and C-terminal fusion strategies can be employed; and 5) APEx can be used directly for proteins expressed from popular phage display vectors. This latter point is particularly important because it enables hybrid library screening strategies, in which clones from a phage panning experiment can be quantitatively analyzed or sorted further by flow cytometry without the need for any subcloning steps.

Figure 1B:
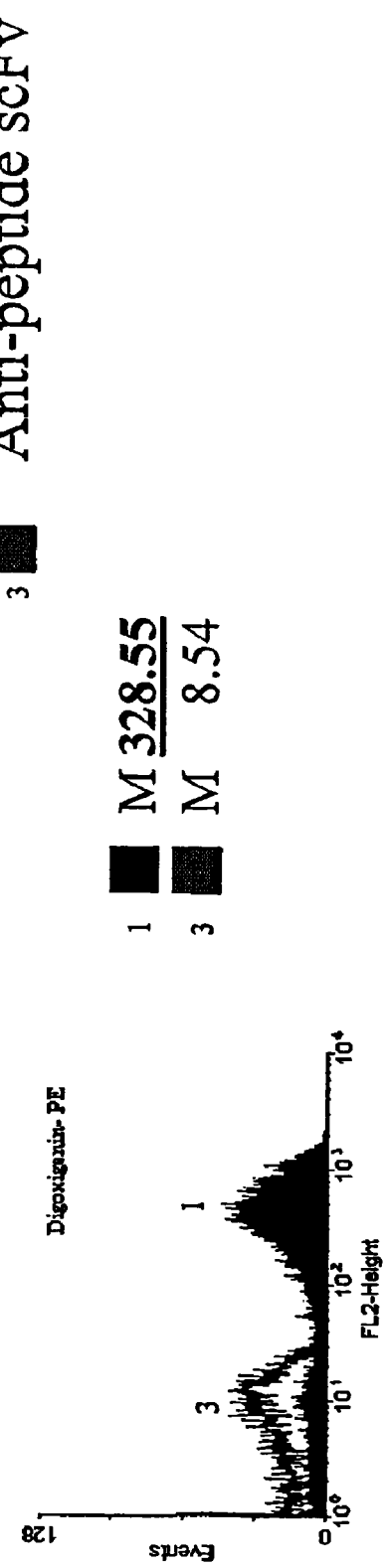

APEx can be employed for the detection of antigens ranging from small molecules (e.g. digoxigenin and methamphetamine <1 kDa) to phycoerythrin conjugates (240 kDa). In fact, the phycoerythrin conjugate employed in FIG. 1B is not meant to define an upper limit for antigen detection, as it is contemplated that larger proteins may be used as well.

In the example, genes encoding scFvs that bind the fluorescently labeled antigen, were rescued from the sorted cells by PCR™. An advantage of this approach is that it enables the isolation of clones that are no longer viable due to the combination of potential scFv toxicity, Tris-EDTA-lysozyme disruption, and FC shear forces. In this way, diversity of isolated clones is maximized. Yet another advantage of PCR™ rescue is that the amplification of DNA from pooled cells can be carried out under mutagenic conditions prior to subcloning. Thus, following each round of selection random mutations can be introduced into the isolated genes, simplifying further rounds of directed evolution (Hanes and Pluckthun, 1997). Further, PCR™ conditions that favor template switching among the protein encoding genes in the pool may be employed during the amplification step to allow recombination among the selected clones. It is likely that PCR™ rescue would be advantageous in other library screening formats as well.

An important issue with any library screening technology is the ability to express isolated clones at a high level. Existing display formats involve fusion to large anchoring sequences which can influence the expression characteristics of the displayed proteins. For this reason, scFvs that display well may not necessarily be amenable to high expression in soluble form as non-fusion proteins (Hayhurst et al., 2003). In contrast, the short (6 amino acid) tail that may be used for N-terminal tethering of proteins onto the cytoplasmic membrane in the current invention is unlikely to affect the expression characteristics of the fusion. Consistent with this hypothesis, all three affinity enhanced clones to the anthrax PA toxin isolated by APEx exhibited excellent soluble expression characteristics despite having numerous amino acid substitutions. Similarly, well-expressing clones have been obtained in the affinity maturation of a methamphetamine antibody, suggesting that the isolation of clones that can readily be produced in soluble form in bacteria at a large scale might be an intrinsic feature of selections with the invention.

In this example, the inventors employed APEx for affinity maturation purposes and have engineered scFvs to the *B. anthracis* protective antigen exhibiting $K_D$ values as low as 21 pM. The scFv binding site exhibiting the highest affinity for PA has been humanized, converted to full length IgG and its neutralizing potential to anthrax intoxication is being evaluated in preclinical studies. In addition to affinity maturation, APEx can be exploited for several other protein engineering applications including the analysis of membrane protein topology, whereby a scFv antibody anchored in a periplasmic loop is able to bind fluorescent antigen and serves as a fluorescent reporter, and also, the selection of enzyme variants with enhanced function. Notably, APEx can be readily adapted to enzyme library sorting, as the cell envelope provides sites for retention of enzymatic catalytic products, thereby enabling selection based directly on catalytic turnover (Olsen et al., 2000). The inventors are also evaluating the utilization of APEx for the screening of ligands to membrane proteins. In conclusion, it has been demonstrated that anchored periplasmic expression has the potential to facilitate combinatorial library screening and other protein engineering applications.

Example 3

Recombinant DNA Techniques

The leader peptide and first six amino acids of the mature N1pA protein flanked by NdeI and SfiI sites was amplified by whole cell PCR of XL1-Blue (Stratagene, CA) using primers BRH#08 5'-GAAGGAGATATACATATGAAACTGACAA-CACATCATCTA-3' (SEQ ID NO:6) and BRH#09 5'-CTGGGCCATGGCCGGCTGGGCCTCGCT-GCTACTCTGGTCGCAACC-3' (SEQ ID NO:7). The resulting N1pA fragment was used to replace the pelB leader sequence of pMoPac1 (Hayhurst et al., 2003) via NdeI and SfiI to generate pAPEx1. scFv specific for digoxin (Chen et al., 1999), *Bacillus anthracis* protective antigen PA (Maynard et al., 2002) and methamphetamine were inserted downstream of the N1pA fragment in pAPEx1 via the non-compatible SfiI sites. Corresponding g3p fusions of the scFv were made by cloning the same genes into phage display vector pAK200 (Krebber et al., 1997).

Example 4

Growth Conditions

*E. coli* ABLE C™ (Stratagene) was the host strain used throughout. *E. coli* transformed with the pAPEx1 or pAK$^2$00 derivatives were inoculated in terrific broth (TB) supplemented with 2% glucose and chloramphenicol at 30 ug/ml to an OD600 of 0.1. Cell growth and induction were performed as described previously (Chen et al., 2001). Following induction, the cellular outer membrane was permeabilized as described (Neu and Heppel, 1965). Briefly, cells (equivalent to approx 1 ml of 20 OD600) were pelleted and resuspended in 350 µl of ice-cold solution of 0.75M sucrose, 0.1M Tris-HCl pH8.0, 100 µg/ml hen egg lysozyme. 700 µl of ice-cold 1 mM EDTA was gently added and the suspension left on ice for 10 min. 50 µt of 0.5M $MgCl_2$ was added and the mix left on ice for a further 10 min. The resulting cells were gently pelleted and resuspended in phosphate buffered saline (1× PBS) with 200 nM probe at room temperature for 45 min, before evaluation by FC.

Example 5

Fluorescent Probe

The synthesis of digoxigenin-BODIPY has been described previously (Daugherty et al., 1999). Methamphetamine-fluorescein conjugate was a gift from Roche Diagnostics. Purified PA protein kindly provided by S. Leppla NIH, was conjugated to BODIPY™ at a 1 to 7 molar ratio with bodipy FL SE D-2184 according to the manufacturers instructions. Unconjugated BODIPY™ was removed by dialysis.

To synthesize digoxigenin-phycoerythrin, R-phycoerythrin and 3-amino-3-dioxydigxigenin hemisuccinamide, succinimidyl ester (Molecular Probes) were conjugated at a 1 to 5 molar ratio according to the manufacturers instructions. Free digoxigenin was removed by dialysis in excess PBS.

Example 6

Affinity Maturation of scFv Libraries with FC

Libraries were made from the 14B7 parental scFv using error prone PCR using standard techniques (Fromant et al., 1995) and cloned into the pAPEx1 expression vector. Upon transformation, induction and labeling the cells were then stained with propidium iodide (PI emission 617 nm) to monitor inner membrane integrity. Cells were analyzed on a MoFlo (Cytomation) droplet deflection flow cytometer using 488 nm Argon laser for excitation. Cells were selected based on improved fluorescence in the Fluorescein/Bodipy FL emission spectrum detecting through a 530/40 band pass filter and for the absence of labeling in PI emission detecting through a 630/40 band pass filter.

*E. coli* captured after the first sort were immediately resorted through the flow cytometer. Subsequently, the scFv genes in the sorted cell suspension were amplified by PCR™. Once amplified, the mutant scFv genes were then recloned into pAPEx1 vector, retransformed into cells and then grown overnight on agar plates at 30° C. The resulting clones were subjected to a second round of sorting plus resorting as above, before scFv genes were subcloned into pMoPac16 (Hayhurst et al., 2003) for expression of scAb protein.

Example 7

Surface Plasmon Resonance Analysis

Monomeric scAb proteins were purified by IMAC/size-exclusion FPLC as described previously (Hayhurst et al., 2003). Affinity measurements were obtained via SPR using a BIACore3000 instrument. Approximately 500RUs of PA was coupled to a CM5 chip using EDC/NHS chemistry. BSA was similarly coupled and used for in line subtraction. Kinetic analysis was performed at 25° C. in BIA HBS-EP buffer at a flow rate 100 µl/min. Five two fold dilutions of each antibody beginning at 20 nM were analyzed in triplicate.

Example 8

Maximizing the Fluorescence Signal

The fluorescence intensity of cells expressing scFv antibodies in soluble form in the periplasm was strongly dependent on the *E. coli* strain used and on the growth conditions. With a 26-10 antibody, the maximum fluorescence intensity was obtained when the cells were grown at 25° C. Growth at sub-physiological temperature has several beneficial effects. Expression of scFv at low temperature (i.e., 25° C.) facilitates the proper folding of the scFv both directly, by slowing the folding pathway and indirectly by decreasing plasmid copy number to reduce expression load. Indeed, direct expression of scFv at 37° C. generally yields little or no soluble protein (for example see Gough et al., 1999). Outer membrane composition is also altered at non-physiological temperatures resulting in increased permeability (Martinez et al., 1999). Rather dramatic differences among various *E. coli* strains were noticed. Among several strains tested, the highest fluorescence intensities were obtained in ABLE™C. A preliminary analysis of protein expression and outer membrane protein profile in this strain indicated that the higher fluorescent signal was not due to the pcnB mutation which reduces the copy number of ColE1 origin plasmids but rather, due to differences in cell envelope protein composition. In fact, the stronger staining of ABLE™C was not related to a higher level of protein expression relative to other strains as deduced by ELISA and Western blotting.

Fluorescent labeling under hyperosmotic conditions, resulted in significantly greater fluorescence. A 5-7 fold increase in fluorescence was obtained when the cells were incubated in 5× PBS during labeling (a mean FL1>150 compared to 20-30 for cells incubated in regular PBS). However, the increased signal came at a cost, as cell viability decreased considerably. Such a decrease in viability may be undesirable when screening highly diverse libraries of proteins, whose expression may already have a deleterious effect on the host cell. Similarly, co-infection with filamentous phages such as M13KO7 induces the phage shock response, which among other things, results in an increase in outer membrane permeability. M13 KO7 infection resulted in a 3-fold increase in the mean fluorescence of the population. However, as with hyperosmotic shock the viability of the culture, as determined by propidium iodide staining was somewhat decreased.

Labeling of the cells with fluorescent ligand followed by incubation with a large excess of free ligand results in a time-dependent decrease in the mean fluorescence intensity. The rate of the fluorescence decay reflects the dissociation rate of the antibody-antigen complex (Daugherty et al., 2000). For digoxin, the rate of fluorescence decay was found to be about 3-4 times slower compared to the dissociation rate measured with the purified antibody using BIACORE. The lower rate of fluorescence decay compared to the dissociation rate of the antibody/antigen complex in vitro stems from several effects including the collision frequency between ligands and cells, the concentration of antibody in the periplasm and, of course, the rate of diffusion through the outer membrane (see Martinez et al., 1996) for an analysis of kinetics in the periplasmic space). As may be expected, the ratio of the rate of fluorescence decay in the periplasm relative to the in vitro determined $k_{off}$ rate is antigen dependent.

Example 9

Increased Cell Permeability at Sub-Optimum Temperature

The fluorescence intensity of cells expressing scFv antibodies in soluble form in the periplasm was strongly dependent on the E. coli strain used and on the growth conditions. With a 26-10 antibody, the maximum fluorescence intensity was obtained when the cells were grown at 25° C. Growth at sub-physiological temperature has several beneficial effects. Expression of scFv at low temperature (i.e., 25° C.) facilitates the proper folding of the scFv both directly, by slowing the folding pathway and indirectly by decreasing plasmid copy number to reduce expression load. Indeed, direct expression of scFv at 37° C. generally yields little or no soluble protein (for example see Gough et al., 1999). Outer membrane composition is also altered at non-physiological temperatures resulting in increased permeability (Martinez et al., 1999). Rather dramatic differences among various E. coli strains were noticed. Among several strains tested, the highest fluorescence intensities were obtained in ABLE™C. A preliminary analysis of protein expression and outer membrane protein profile in this strain indicated that the higher fluorescent signal was not due to the pcnB mutation which reduces the copy number of ColE1 origin plasmids but rather, due to differences in cell envelope protein composition. In fact, the stronger staining of ABLE™C was not related to a higher level of protein expression relative to other strains as deduced by ELISA and Western blotting.

Fluorescent labeling under hyperosmotic conditions, resulted in significantly greater fluorescence. A 5-7 fold increase in fluorescence was obtained when the cells were incubated in 5× PBS during labeling (a mean FL1>150 compared to 20-30 for cells incubated in regular PBS). However, the increased signal came at a cost, as cell viability decreased considerably. Such a decrease in viability may be undesirable when screening highly diverse libraries of proteins, whose expression may already have a deleterious effect on the host cell. Similarly, co-infection with filamentous phages such as M13KO7 induces the phage shock response, which among other things, results in an increase in outer membrane permeability. M13 KO7 infection resulted in a 3-fold increase in the mean fluorescence of the population. However, as with hyperosmotic shock the viability of the culture, as determined by propidium iodide staining was somewhat decreased.

Labeling of the cells with fluorescent ligand followed by incubation with a large excess of free ligand results in a time-dependent decrease in the mean fluorescence intensity. The rate of the fluorescence decay reflects the dissociation rate of the antibody-antigen complex (Daugherty et al., 2000). For digoxin, the rate of fluorescence decay was found to be about 3-4 times slower compared to the dissociation rate measured with the purified antibody using BIACORE. The lower rate of fluorescence decay compared to the dissociation rate of the antibody/antigen complex in vitro stems from several effects including the collision frequency between ligands and cells, the concentration of antibody in the periplasm and, of course, the rate of diffusion through the outer membrane (see Martinez et al., 1996) for an analysis of kinetics in the periplasmic space). As may be expected, the ratio of the rate of fluorescence decay in the periplasm relative to the in vitro determined $k_{off}$ rate is antigen dependent.

Example 10

Analysis and Screening of Repertoire Antibody Libraries by FACS

Antibodies can be isolated de novo; i.e., without animal immunization, by screening large, repertoire libraries that contain a wide variety of antibody sequences. The screening of such large libraries is well established (Nissim et al. 1994, Winter et al. 1994, Griffith et al. 1994, Knappik et al. 2000). So far, all the large antibody repertoire libraries available have been constructed for use with phage display. However, libraries constructed for phage display can also be used for the expression of proteins within the bacterial periplasmic space, either anchored to the inner membrane or in soluble form. In particular, for low protein copy number display on filamentous bacteriophage, recombinant polypeptides are expressed as N-terminal fusions to pIII. During the course of phage biogenesis, pm fusions are first targeted to the periplasm and anchored in the inner membrane by a small C-terminal portion of pil. As phage are released, the scFv-plH fusion is incorporated alongside wild-type pii at the terminus of the phage, thereby concluding the assembly process (Rakonjac and Model, 1998; Rakonjac et al., 1999). In the most widely used vectors for phage display, an amber codon is placed between the N-terminal scFv and the pIII gene. Thus, in a suitable *E. coli* suppressor strain, full-length scFv-pIII fusion protein is produced for displaying the scFv whereas in a non-supressor strain only soluble scFv is expressed. Alternatively, by including an inner membrane anchor peptide in the fusion, anchored expression can be achieved.

The degree of suppression with phage display varies with vector and strain but tends to allow only 10% read-through. Thus, as a consequence of the biology of phage display, all amber-codon containing libraries result in a degree of periplasmic expression regardless of host. Hence, it was of great interest to explore whether FACS can aid the isolation of ligand binding proteins from pre-existing, highly diverse, naive libraries (Griffith et al., 1994; Vaughan et al., 1996; Sheets et al., 1998; Pini et al., 1998; de Haard et al., 1999; Knappik et al., 2000; Sblattero and Bradbury, 2000).

Conventional screening was performed of a phage library by phage panning enriched phage expressing scFvs specific for the cardiac glycoside digoxin from a naive antibody repertoire library. The panning process was performed on a BSA conjugate and the screening was performed on an ovalbumin conjugate to reduce the incidence of protein and hapten-protein interface binders. 24 positive isolates from pan 4 shared the same fingerprint and DNA sequencing of 6 clones confirmed the same heavy and light chain sequence ("dig1") with one of six ("dig2") having a unique HCDR3 and LCDR3 combination. Repeated screening of the phage library both under identical and under different conditions resulted only in the isolation of clones with the same DNA fingerprint.

FACS analysis of the phage rescued in *E. coli* ABLE™C after each round of panning reveals an increase in mean fluorescence at round 3 which mirrors the phage ELISA signals. Significant enrichment of binding clones using a single round of FACS was obtained starting with the population obtained from the $3^{rd}$ round of phage panning. This result is consistent with the enrichment profiles obtained during the course of the panning experiment. FACS screening and sorting $10^6$ cells from rounds 3, 4 and 5 resulted in the isolation of positive clones at a frequency of 30, 80 and 100% respectively.

Out of 14 clones isolated by FACS from the round 3 population, 5 were found to be positive for binding to digoxin. Importantly, three of the clones corresponded to a different antibody that was missed by phage panning (herein known as "dig3"). The remaining 2 were the dig1 clone. This result demonstrates that FACS screening of libraries expressed in the periplasmic space and labeled with fluorescent ligands results in the isolation of clones that cannot be isolated by other library screening methodologies.

Example 11

Flow Cytometric Discrimination of *E. coli* Expressing the *Fusarium solani* Lipase Cutinase Using Commercial Fluorescent Substrates This example demonstrates that commercially available fluorescent substrates can be used to specifically label *E. coli* cells displaying relevant enzymes in the periplasm. Surprisingly, the soluble fluorescent product of these reactions is sufficiently retained within the cell to allow for the discrimination and selection of enzyme expressing *E. coli* from non-enzyme expressing bacteria.

The gene encoding *Fusarium solani* lipase cutinase was constructed by total gene synthesis and placed downstream of the strong inducible promoter pBAD in plasmid pBAD18Cm. Protein expression from the pBAD promoter is beneficial for the screening of protein libraries by FACS (Daugherty et al. 1999). The resulting plasmid encoding the cutinase gene was designated pKG3-53-1. pKG3-53-1, and pBAD18Cm as a control, were both transformed into DH5a. In this example, the ability to discriminate cells expressing cutinase (DH5a (pKG3-53-1)) from control cells was determined using two different commercially available substrates: Fluorescein dibutyrate or LysoSensor Green DND-189 (LSG) (both from Molecular Probes, OR). The latter is a positively charged fluorescent probe that detects pH changes in the cell occurring due to ester hydrolysis by the enzyme.

Cells were grown overnight with vigorous shaking at 37oC in terrific broth/chloramphenicol 50 μg/ml (TB/Cm). Subcultures were made from 100 μl of overnight culture in 10 ml of TB/Cm(50 μg/ml). These subcultures were grown with vigorous shaking at 37° C. to $OD_{600}$=0.6. Four ml aliquots of the subcultures were pelleted at 3650 rpm for 20 minutes in a Beckman Allegra 6R Centrifuge. The supernatant was removed, and the pellets were resuspended in 4 ml of M9 minimal media containing 0.2% glucose and chloramphenicol (Cm) at 50 μg/ml. Arabinose, from a 20% stock, was added to a final concentration of 0.2%. The cultures were induced at 25° C. with vigorous shaking for 4 hours. Subsequently, 2 ml. aliquots of the induced cultures were pelleted at 8000 rpm for 10 minutes in an Eppendorf 5415C Centrifuge, washed with fresh media and pelleted again at 8000 rpm for 10 min. The washed pellets were resuspended in M9 salts media without glucose to an optical density $OD_{600}$=1.0. The stock solution was diluted 1:10 and 1 ml of the diluted cell suspension was mixed with 0.1 ml 0.1 mM Fluorescein dibutyrate (FDB) stock solution in dimethyl sulfoxide (DMSO). The final FDB concentration was 10 μM. Reactions were allowed to proceed at 37° C. for 30 minutes. The labeled cells were immediately analyzed on a Becton Dickinson FACSort equipped with an Ar 488 nm laser. The fluorescence distribution of the cutinase expressing cells and the control cells is shown in FIG. 4A.

The utility of a second probe for the discrimination between positive (enzyme expressing) and control cells was also examined. *E. coli* expressing cutinase from the pKG3-53-4 plasmid, and negative cells (expressing the umnodified pBAD18Cm plasmid) were grown, induced and washed as above. The pellet was washed with 1% sucrose, pelleted again, and resuspended in fresh 1% sucrose to $OD_{600}$=1.0. This stock solution of cells was kept on ice.

For labeling, a LysoSensor Green DND-189 (LSG, Molecular Probes) stock solution was prepared to 1 mM in DMSO. Also, a 1 M 4-Nitrophenyl Butyrate stock solution was prepared in DMSO. Cell labeling was initiated by first diluting the cell stock solution, adding the LSG to a final concentration of 1 μM and diluting the 4-Nitrophenyl Butyrate 1:1000 to give a final concentration of 1 μM. The enzymatic hydrolysis of 4-Nitrophenyl Butyrate by the cells was allowed to proceed at 25° C. for 5 minutes and the cells were then immediately analyzed on a Becton Dickinson FACSort as above.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbondanzo et al., *Am J Pediatr Hematol Oncol*, 12(4):480-9, 1990.
Atherton et al., *Biol. of Reproduction*, 32:155, 1985.
Ausubel et al., *In: Current Protocols in Molecular Biology*, John, Wiley & Sons, Inc, New York, 1994.
Barbas et al., *Proc. Natl. Acad. Sci. USA*, 88:7978-7982, 1991.
Bellus, *J. Macromol. Sci. Pure Appl. Chem.*, RS3241(1): 1355-1376, 1994.
Berrier et al., *J. Bacteriol.*, 182:248, 2000.
Boder and Wittrup, *Methods Enzymol.*, 328:430-444, 2000.
Boder et al., *Proc. Natl. Acad. Sci. USA*, 97:10701-10705, 2000.
Boeke and Model, *Proc. Natl. Acad. Sci. USA*, 79:5200-5204, 1982.
Bradley et al., *Nature*, 8;414(6860):225-229, 2001.
Burioni et al., *Res. Virol.*, 149:327, 1998.
Burnan et al., *J. Bacteriol.*, 112:1364, 1972.
Carbonelli et al., *FEMS Microbiol. Lett.*, 177(1):75-82, 1999.
Chen and Okayama, *Mol. Cell Biol.*, 7(8):2745-2752, 1987.
Chen et al., *Nat. Biotechnol.*, 19:537-542, 2001.
Chen et al., *Protein Eng.*, 12:349-356, 1999.
Chowdhury and Pastan, *Nat. Biotech.*, 17:568, 1999.
Cocea, *Biotechniques*, 23(5):814-816, 1997.
Coia et al., *Gene* 201:203, 1997.
Corey et al., *Gene*, 128:129, 1993.
Dall'Acqua and Carter, *Curr. Opin. Struct. Biol.*, 8:443, 1998.
Daugherty et al., *J. Immunol. Methods.* 243:211, 2000.
Daugherty et al., *Proc. Natl Acad. Sci. USA*, 97:2029-2034, 2000.
Daugherty et al., *Protein Eng.*, 12:613-621, 1999.
De Haard et al., *J. Biol. Chem.*, 274:18218, 1999.
De Jager R et al., *Semin Nucl Med* 23:165, 1993.
De Wildt et al., *Nat. Biotechnol.* 18:, 989, 2000.
Decad and Nikaido, *J. Bacteriol.*, 128:325, 1976.
Deng et al., *J. Biol. Chem.*, 269:9533, 1994.
Deng et al., *Proc. Natl. Acad. Sci. USA*. 92:4992, 1995.
Dholakia et al., J. Biol. Chem., 264, 20638-20642, 1989.
Dixon et al., *New England Journal of Medicine*, 341:815-26, 1999.
Doolittle M H and Ben-Zeev O, *Methods Mol Biol.*, 109:215, 1999.
Duenas and Borrebaeck, *Biotechnology*, 12:999, 1994.
Fechheimer et al., *Proc. Natl. Acad. Sci. USA*, 84:8463-8467, 1987.
Fraley et al., *Proc. Natl. Acad. Sci. USA*, 76:3348-3352, 1979.
Frohman, *In: PCR PROTOCOLS: A GUIDE TO METHODS AND APPLICATIONS*, Academic Press, N.Y., 1990.
Fromant et al., *Anal. Biochem.*, 224:347-353, 1995.
Georgiou et al., *Nat. Biotechnol.* 15:29, 1997.
Gopal, *Mol. Cell. Biol.*, 5:1188-1190,1985.
Gough et al., *J. Immunol. Met.*, 228:97, 1999.
Graham and Van Der Eb, *Virology*, 52:456-467, 1973.
Griep et al., *Prot. Exp. Purif.*, 16:63, 1999.
Griffith et al., *EMBO J.*, 13: 3245, 1994.
Gulbis and Galand, *Hum Pathol* 24:1271, 1993.
Hanes and Pluckthun, *Proc. Natl. Acad. Sci. USA*, 94:4937-4942, 1997.
Harland and Weintraub, *J. Cell Biol.*, 101:1094-1099, 1985.
Hayhurst and Georgiou, *Curr. Opin. Chem. Biol.*, 5:683-689, 2001.
Hayhurst and Harris, *Protein Expr. Purif.:*, 15:336-343, 1999.
Hayhurst et al., *J. Immunol. Methods*, 276:185-196, 2003.
Hayhurst, *Protein Expr. Purif.:*, 18:1-10, 2000.
Hobot et al., *J. Bacteriol.* 160:143, 1984.
Hoess, *Chem. Rev.*, 101:3205-3218, 2001.
Hoogenboom et al., *Adv. Drug. Deliv. Rev.*, 31:5, 1998.
Hudson, *Curr. Opin. Biotechnol.*, 9:395, 1998.
Hultgren et al., *Bacterial Adhesins Assembly*, Vol.-2., 1996.
Innis et al., *Proc Natl Acad Sci USA*, 85:9436, 1988.
Johns et al., *J. Immunol. Methods*, 239:137, 2000.
Kaeppler et al., *Plant Cell Reports* 9: 415-418, 1990.
Kaneda et al., *Science*, 243:375-378, 1989.
Kato et al, *J. Biol. Chem.*, 266:3361-3364, 1991.
Keller and Stiehlm, *Clin. Microbiol. Reviews*, 13:602-614, 2000.
Khatoon et al., *Ann. of Neurology*, 26, 210-219, 1989.
King et al., *J. Biol. Chem.*, 269:10218, 1989.
Kjaer et al., *FEBS Lett.*, 431:448, 1998.
Knappick et al., *J. Mol. Biol.*, 296:57, 2000.
Krebber et al., *Gene*, 178:71, 1996.
Krebber et al., *J. Immunol. Methods*, 201:35-55, 1997.
Kwoh et al, *Proc Natl Acad Sci USA*. 86:1173, 1989.
Labischinski et al., *J Bacteriol.*, 162:9, 1985.
Levenson et al., *Hum. Gene Ther.*, 9(8):1233-1236, 1998.
Levitan, *J. Mol. Biol.*, 277:893, 1998.
Li et al., *Nat. Struct. Biol.*, 10:482-488, 2003.
MacKenzie and To, *J. Immunol. Methods*, 220:39, 1998.
MacKenzie et al., *J. Biol. Chem.*, 271:1527, 1996.
Maenaka et al., *Biochem Biophys Res Commun.*, 218:682, 1996.
Malmborg et al., *J. Immunol. Methods*, 198:51, 1996.
Maniatis, et al., Molecular Cloning, A Laboratory Manual, Cold Spring Harbor Press, Cold Spring Harbor, N.Y., 1988.
Marks et al., *Bio/Technol.* 10:779, 1992.
Martinez et al., *Biochemistry*, 35:1179, 1996.
Martinez et al., *J. Biotechnol.*, 71:59, 1999.
Maynard et al., *Nat. Biotechnol.*, 20:597-601, 2002.
Mingarro et al., *Trends Biotechnol.*, 15:432-437, 1997.
Miroux and Walker, *J. Mol. Biol.*, 260:289-298, 1996.
Morrison, et al., *Proc. Nat'l. Acad. Sci USA*. 81:6851, 1984.
Munson & Pollard, Anal. Biochem. 107:220, 1980.
Mutuberria et al., *J. Immunol. Methods*, 231:65, 1999.
Nakae, *J. Biol. Chem.*, 251:2176, 1976.
Neu and Heppel, *J. Biol. Chem.*, 240:3685-3692, 1965.
Nicolau and Sene, *Biochim. Biophys. Acta*, 721:185-190, 1982.
Nicolau et al., *Methods Enzymol.*, 149:157-176, 1987.
Nikaido and Nakae, *Adv. Microb. Physiol.*, 20:163, 1979.
Nikaido and Vaara, *Microbiol. Rev.* 49:1, 1985.
Nissim et al., *EMBO J.*, 13:692, 1994.
Ohara et al., "One-sided polymerase chain reaction: the amplification of cDNA,"
Olsen et al., *Nat. Biotechnol*, 18:1071-1074, 2000.
Omirulleh et al., *Plant Mol. Biol.*, 21(3):415-28, 1993.
Owens & Haley, *J. Biol. Chem.*, 259:14843-14848, 1987.
PCT Application WO 93/06213
PCT Application WO 94/09699
PCT Application WO 95/06128
PCT Applicaton WO 90/07641
Pini et al., *J. Biol. Chem.*, 273:21769, 1998.
Potrykus et al., *Mol. Gen. Genet.*, 199:183-188,1985.
Potter & Haley, *Meth. in Enzymol.*, 91, 613-633, 1983.

Pugsley, *Microbiol. Rev.,* 57:50-108, 1993.
Rakonjac and Model, *J. Mol. Biol.,* 282:25, 1998.
Rakonjac et al., *J. Mol. Biol.,* 289:1253, 1999.
Rippe et al., *Mol. Cell Biol.,* 10:689-695, 1990.
Rodi and Makowski, *Curr. Opin. Biotechnol.,* 10:87-93, 1999.
Sagt et al., *Appl. Environ. Microbiol.,* 68:2155-2160, 2002.
Sambrook et al., *In: Molecular Cloning: A Laboratory Manual,* Vol. 1, Cold Spring Harbor Laboratory Press, Cold Spring Harbor, N.Y., Ch. 7, 7.19-17.29, 1989.
Samuelson et al., *Nature,* 406:637-641, 2000.
Sblattero and Bradbury, *Nat. Biotechnol.,* 18:75, 2000.
Seydel et al., *Mol. Microbiol.,* 34:810-821, 1999.
Shafazand, *Chest,* 116(5): 1369-76, 1999.
Sheets et al., *Proc. Natl Acad. Sci. USA.,* 95:6157, 1998.
Shusta et al., *J. Mol. Biol.,* 292:949, 1999.
Somerville et al., *Appl. Microbiol. Biotechnol.,* 42:595-603, 1994.
Thompson et al., *J. Mol. Biol.* 256, 77, 1999.
Thorstenson et al., *J. Bacteriol.,* 179:5333, 1997.
Van Wielink and Duine, *Trends Biochem Sci.,* 15:136, 1990.
Vaughan et al., *Nat. Biotechnol.,* 14:309, 1996.
Walker et al., *Nucleic Acids Res.* 20:1691, 1992
Waterhouse et al., Nucl. Acids Res. 21, 2265-2266 (1993)
Winter et al, *Ann. Rev. Immunol.* 12: 433, 1994.
Wittrup, *Nat. Biotechnol.,* 18:1039-1040, 2000.
Wong et al., *Gene,* 10:87-94, 1980.
Wu et al., *Biochem Biophys Res Commun.* 233:221, 1997.
Yajkushi et al., *Nat. Cell. Biol.,* 2:212-218, 2000.
Yamaguchi et al., *Cell,* 53:423-432, 1988.
Yu et al., *J. Biol. Chem.,* 261:2284-2288, 1986.

---

What is claimed is:

1. An isolated nucleic acid encoding an isolated antibody or fragment thereof that binds immunologically to *Bacillus anthracis* protective antigen and comprises the variable light and variable heavy chain of SEQ ID NO:21, with the exception that the variable light and variable heavy chain collectively comprise at least three modifications selected from the group consisting of: I21V, S22G, L33S, Q38R, L46F, Q55L, S56P, T74A, S76N, Q78L, L94P, S7P, K19R, S30N, T57S, K62R, K64E, T68I, and M80L; wherein said I21V, S22G, L33S, Q38R, L46F, Q55L, S56P, T74A, S76N, Q78L and L94P are in the variable light chain and wherein said S7P, K19R, S30N, T57S, K62R, K64E, T68I and M80L are in the variable heavy chain.

2. The isolated nucleic acid of claim 1, further defined as encoding the variable light chain of SEQ ID NO:23 or SEQ ID NO:25.

3. The isolated nucleic acid of claim 1, further defined as encoding the variable heavy chain of SEQ ID NO:23 or SEQ ID NO:25.

4. The isolated nucleic acid of claim 1, further defined as encoding the polypeptide of SEQ ID NO:23.

5. The isolated nucleic acid of claim 1, further defined as encoding the polypeptide of SEQ ID NO:25.

* * * * *

UNITED STATES PATENT AND TRADEMARK OFFICE
CERTIFICATE OF CORRECTION

| | | |
|---|---|---|
| PATENT NO. | : 7,902,344 B2 | Page 1 of 1 |
| APPLICATION NO. | : 11/179244 | |
| DATED | : March 8, 2011 | |
| INVENTOR(S) | : Barrett R. Harvey et al. | |

It is certified that error appears in the above-identified patent and that said Letters Patent is hereby corrected as shown below:

In title page, item (56) References Cited - FOREIGN PATENT DOCUMENTS, insert
--WO      WO 99/36569      1/1999--.

Signed and Sealed this

Twenty-sixth Day of July, 2011

David J. Kappos
*Director of the United States Patent and Trademark Office*

SEQUENCE LISTING

```
<160> NUMBER OF SEQ ID NOS: 25

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 1
caggaaacag ctatgac                                                       17

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 2
gaattttctg tatgagg                                                       17

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 3
gccacctccg cctgaacc                                                      18

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:   Synthetic
      Primer

<400> SEQUENCE: 4
ctatgcggcc ccattca                                                       17
```

```
<210> SEQ ID NO 5
<211> LENGTH: 5
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5 aaaaa                                                                      5

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gaaggagata tacatatgaa actgacaaca catcatcta                                39

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ctgggccatg gccggctggg cctcgctgct actctggtcg caacc                         45

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Gln Thr Thr His Val Pro Pro
 1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Gln Thr Thr His Val Pro Pro
 1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Gln Thr Thr His Ser Pro Ala
 1               5
```

```
<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Gln Thr Thr His Leu Pro Thr
  1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Gln Thr Thr His Thr Pro Pro
  1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Gln Thr Thr His Thr Pro Pro
  1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Gln Thr Thr His Ile Pro Thr
  1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Gln Thr Thr His Val Pro Pro
  1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
```

-continued

```
<400> SEQUENCE: 16

Gln Thr Thr His Val Pro Ala
  1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 17

Gln Thr Thr His Ile Pro Ala
  1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 18

Gln Thr Thr His Leu Pro Ala
  1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 19

Gln Thr Thr His Val Pro Cys
  1               5

<210> SEQ ID NO 20
<211> LENGTH: 741
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 20
gatattcaga tgacacagac tacatcctcc ctgtctgcct ctctgggaga cagagtcacc      60
atcagttgca gggcaagtca ggacattagg aattatttaa actggtatca gcagaaacca     120
gatggaactg ttaaactcct gatctactac acatcaagat tacagtcagg agtcccatca     180
aggttcagtg gcagtgggtc tggaacagat tattctctca ccattagcaa ccaggagcaa     240
gaagatattg cacttacttt tgccaacag  ggtaatacgc ttccgtggac gttcggtgga     300
ggcaccaagc tggaaataaa acgtggtggt ggtggttctg gtggtggtgg ttctggcggc     360
ggcggctccg gtggtggtgg atccgaggtc caactgcaac agtctggacc tgagctggtg     420
aagcctgggg cctcagtgaa gatttcctgc aaagattctg gctacgcatt cagtagctct     480
tggatgaact gggtgaagca gaggcctgga cagggtcttg agtggattgg acggatttat     540
cctggagatg gagatactaa ctacaatggg aagttcaagg gcaaggccac actgactgca     600
gacaaatcct ccagcacagc ctacatgcag ctcagcagcc tgacctctgt ggactctgcg     660
```

```
gtctatttct gtgcaagatc ggggttacta cgttatgcta tggactactg gggtcaagga    720
acctcagtca ccgtctcctc g                                              741
```

<210> SEQ ID NO 21
<211> LENGTH: 247
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Tyr Ser Leu Thr Ile Ser Asn Gln Glu Gln
65                  70                  75                  80

Glu Asp Ile Gly Thr Tyr Phe Cys Gln Gln Gly Asn Thr Leu Pro Trp
                85                  90                  95

Thr Phe Gly Gly Gly Thr Lys Leu Glu Ile Lys Arg Gly Gly Gly Gly
            100                 105                 110

Ser Gly Gly Gly Gly Ser Gly Gly Gly Ser Gly Gly Gly Gly Ser
        115                 120                 125

Glu Val Gln Leu Gln Gln Ser Gly Pro Glu Leu Val Lys Pro Gly Ala
130                 135                 140

Ser Val Lys Ile Ser Cys Lys Asp Ser Gly Tyr Ala Phe Ser Ser Ser
145                 150                 155                 160

Trp Met Asn Trp Val Lys Gln Arg Pro Gly Gln Gly Leu Glu Trp Ile
                165                 170                 175

Gly Arg Ile Tyr Pro Gly Asp Gly Asp Thr Asn Tyr Asn Gly Lys Phe
            180                 185                 190

Lys Gly Lys Ala Thr Leu Thr Ala Asp Lys Ser Ser Ser Thr Ala Tyr
        195                 200                 205

Met Gln Leu Ser Ser Leu Thr Ser Val Asp Ser Ala Val Tyr Phe Cys
    210                 215                 220

Ala Arg Ser Gly Leu Leu Arg Tyr Ala Met Asp Tyr Trp Gly Gln Gly
225                 230                 235                 240

Thr Ser Val Thr Val Ser Ser
                245
```

<210> SEQ ID NO 22
<211> LENGTH: 741
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22

```
gatattcaga tgacacagac tacatcctcc ctgtctgcct ctctgggaga cagagtcacc    60
gtcagttgca gggcaagtca ggacattagg aattatttaa actggtatca gcagaaacca   120
gacggaactg ttaaattcct gatctactac acatcaagat tacagccagg agtcccatca   180
```

```
aggttcagtg gcagtgggtc tggaacagat tattccctca ccattaacaa cctggagcag    240
gaagatattg cacttacttt tgccaacagg gcaatacgcc tccgtggacg ttcggtgga     300 ggcaccaagc tggaaataaa acgtggtgga ggtggttctg atggtggtgg ttctggcggc    360
ggcggctccg gtggtggtgg atccgaggtc caactgcaac agtctggacc tgagctggtg    420
aagcctgggg cctcagtgaa gatttcctgc aaagattctg gctacgcatt caatagctct    480
tggatgaact gggtgaagca gaggcctgga cagggtcttg agtggattgg acggatttat    540
cctggagatg gagattctaa ctacaatggg aaattcgagg caaggccat actgactgca     600 gacaaatcct ccagcacagc ctacatgcag ctcagcagcc tgacctctgt ggactctgcg    660
gtctatttct gtgcaagatc ggggttgcta cgttatgcta tggactactg gggtcaagga    720
acctcagtca ccgtctcctc g                                               741

<210> SEQ ID NO 23
<211> LENGTH: 247
<212> TYPE: PRT
<213> ORGANISM: Artificial Sequence
<220> FEATURE:
<223> OTHER INFORMATION: Description of Artificial Sequence:    Synthetic
      Peptide

<400> SEQUENCE: 23

Asp Ile Gln Met Thr Gln Thr Thr Ser Ser Leu Ser Ala Ser Leu Gly
  1               5                  10                  15

Asp Arg Val Thr Val Ser Cys Arg Ala Ser Gln Asp Ile Arg Asn Tyr
             20                  25                  30

Leu Asn Trp Tyr Gln Gln Lys Pro Asp Gly Thr Val Lys Phe Leu Ile
         35                  40                  45

Tyr Tyr Thr Ser Arg Leu Gln Pro Gly Val Pro Ser Arg Phe Ser Gly
     50                  55                  60

Ser Gly Ser Gly Thr Asp Tyr Ser Leu Thr Ile Asn Asn Leu Glu Gln
 65                  70                  75                  80

Glu Asp Ile Gly Thr Tyr Phe Cys Gln Gln Gly Asn Thr Pro Pro Trp
                 85                  90                  95

Thr Phe Gly Gly Gly Thr Lys Leu Glu Ile Lys Arg Gly Gly Gly Gly
            100                 105                 110

Ser Asp Gly Gly Gly Ser Gly Gly Gly Gly Ser Gly Gly Gly Gly Ser
        115                 120                 125

Glu Val Gln Leu Gln Gln Ser Gly Pro Glu Leu Val Lys Pro Gly Ala
    130                 135                 140

Ser Val Lys Ile Ser Cys Lys Asp Ser Gly Tyr Ala Phe Asn Ser Ser
145                 150                 155                 160

Trp Met Asn Trp Val Lys Gln Arg Pro Gly Gln Gly Leu Glu Trp Ile
                165                 170                 175

Gly Arg Ile Tyr Pro Gly Asp Gly Asp Ser Asn Tyr Asn Gly Lys Phe
            180                 185                 190

Glu Gly Lys Ala Ile Leu Thr Ala Asp Lys Ser Ser Ser Thr Ala Tyr
        195                 200                 205

Met Gln Leu Ser Ser Leu Thr Ser Val Asp Ser Ala Val Tyr Phe Cys
    210                 215                 220

Ala Arg Ser Gly Leu Leu Arg Tyr Ala Met Asp Tyr Trp Gly Gln Gly
225                 230                 235                 240

Thr Ser Val Thr Val Ser Ser
                245
```

-continued

```
<210> SEQ ID NO 24
<211> LENGTH: 741
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
gatattcaga tgacacagac tacatcctcc ctgtctgcct ctctgggaga cagagtcacc      60
gtcagttgca gggcaagtca ggacattagg aattatttaa actggtatca gcagaaacca     120
gacggaactg ttaaattcct gatctactac acatcaagat tactgccagg agtcccatca     180
aggttcagtg gcagtgggtc tggaacagat tattccctca ccattaacaa cctggagcag     240
gaagatattg gcacttactt ttgccaacag gcaatacgc ctccgtggac gttcggtgga      300
ggcaccaagc tggaaataaa acgtggtgga ggtggttctg atggtggtgg ttctggcggc     360
ggcggctccg gtggtggtgg atccgaggtc caactgcaac agtctggacc tgagctggtg     420
aagcctgggg cctcagtgaa gatttcctgc aaagattctg gctacgcatt caatagctct     480
tggatgaact gggtgaagca gaggcctgga cagggtcttg agtggattgg acggatttat     540
cctggagatg gagattctaa ctacaatggg aaattcgagg caaggccat actgacagca      600 gacaaatcct ccagcacagc ctacatgcag ctcagcagcc tgacctctgt ggactctgcg     660
gtctatttct gtgcaagatc ggggttgcta cgttatgcta tggactactg gggtcaagga     720
acctcagtca ccgtctcctc g                                               741

<210> SEQ ID NO 25
<211> LENGTH: 247
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

Asp Ile Gln Met Thr Gln Thr Thr Ser Ser Leu Ser Ala Ser Leu Gly
  1               5                  10                  15

Asp Arg Val Thr Val Ser Cys Arg Ala Ser Gln Asp Ile Arg Asn Tyr
             20                  25                  30

Leu Asn Trp Tyr Gln Gln Lys Pro Asp Gly Thr Val Lys Phe Leu Ile
         35                  40                  45

Tyr Tyr Thr Ser Arg Leu Leu Pro Gly Val Pro Ser Arg Phe Ser Gly
     50                  55                  60

Ser Gly Ser Gly Thr Asp Tyr Ser Leu Thr Ile Asn Asn Leu Glu Gln
 65                  70                  75                  80

Glu Asp Ile Gly Thr Tyr Phe Cys Gln Gln Gly Asn Thr Pro Pro Trp
                 85                  90                  95

Thr Phe Gly Gly Gly Thr Lys Leu Glu Ile Lys Arg Gly Gly Gly Gly
            100                 105                 110

Ser Asp Gly Gly Gly Ser Gly Gly Gly Gly Ser Gly Gly Gly Gly Ser
        115                 120                 125

Glu Val Gln Leu Gln Gln Ser Gly Pro Glu Leu Val Lys Pro Gly Ala
    130                 135                 140

Ser Val Lys Ile Ser Cys Lys Asp Ser Gly Tyr Ala Phe Asn Ser Ser
145                 150                 155                 160

Trp Met Asn Trp Val Lys Gln Arg Pro Gly Gln Gly Leu Glu Trp Ile
                165                 170                 175
```

-continued

```
Gly Arg Ile Tyr Pro Gly Asp Gly Asp Ser Asn Tyr Asn Gly Lys Phe
            180             185             190

Glu Gly Lys Ala Ile Leu Thr Ala Asp Lys Ser Ser Ser Thr Ala Tyr
        195             200             205

Met Gln Leu Ser Ser Leu Thr Ser Val Asp Ser Ala Val Tyr Phe Cys
    210             215             220

Ala Arg Ser Gly Leu Leu Arg Tyr Ala Met Asp Tyr Trp Gly Gln Gly
225             230             235             240

Thr Ser Val Thr Val Ser Ser
            245
```